United States Patent
Garcia et al.

(10) Patent No.: US 10,786,281 B2
(45) Date of Patent: Sep. 29, 2020

(54) RETRACTABLE BURR HOLE PLATE AND METHOD

(71) Applicant: Biomet Manufacturing, LLC, Warsaw, IN (US)

(72) Inventors: Saddy Garcia, St. Augustine, FL (US); Howard Chandler, Jacksonville, FL (US); Scott Sidwell, Jacksonville, FL (US); Adam Hausman, Jacksonville, FL (US); Jacob Mayworth, Jacksonville, FL (US)

(73) Assignee: Biomet Manufacturing, LLC, Warsaw, IN (US)

( * ) Notice: Subject to any disclaimer, the term of this patent is extended or adjusted under 35 U.S.C. 154(b) by 336 days.

(21) Appl. No.: 14/786,431

(22) PCT Filed: Apr. 24, 2014

(86) PCT No.: PCT/US2014/035321
§ 371 (c)(1),
(2) Date: Oct. 22, 2015

(87) PCT Pub. No.: WO2014/176437
PCT Pub. Date: Oct. 30, 2014

(65) Prior Publication Data
US 2016/0143664 A1    May 26, 2016

Related U.S. Application Data

(60) Provisional application No. 61/816,086, filed on Apr. 25, 2013.

(51) Int. Cl.
*A61B 17/80* (2006.01)
*A61B 17/68* (2006.01)
*A61B 90/00* (2016.01)

(52) U.S. Cl.
CPC .......... *A61B 17/688* (2013.01); *A61B 17/808* (2013.01); *A61B 17/8061* (2013.01); *A61B 17/8085* (2013.01); *A61B 90/39* (2016.02)

(58) Field of Classification Search
CPC ............... A61B 17/688; A61B 17/80–17/8095
See application file for complete search history.

(56) References Cited

U.S. PATENT DOCUMENTS

| 434,753 A | * | 8/1890 | Barrows | ................. A47K 13/12 4/236 |
| 1,486,169 A | * | 3/1924 | Trautschold | .............. E04G 1/34 182/155 |

(Continued)

FOREIGN PATENT DOCUMENTS

| WO | WO 2008029143 A2 | * | 3/2008 | ......... A61B 17/7044 |
| WO | WO 2007146541 A9 | * | 8/2008 | ........... A61B 17/688 |
| WO | 2014176437 | | 10/2014 | |

OTHER PUBLICATIONS

"International Application Serial No. PCT/US2014/035321, International Search Report dated Oct. 27, 2014", 5 pgs.

(Continued)

*Primary Examiner* — Zade Coley
(74) *Attorney, Agent, or Firm* — Schwegman Lundberg & Woessner, P.A.

(57) ABSTRACT

A plate assembly for attaching a bone flap to a skull is provided and may include a first plate member attached to the bone flap and a second plate member supported by the first plate member and movable between a retracted position and an extended position relative to the first plate member. The second plate member may be removed from a cut line between the bone flap and the skull in the retracted position and may extend over the cut line in the extended position.

7 Claims, 19 Drawing Sheets

(56) References Cited

U.S. PATENT DOCUMENTS

| | | | | |
|---|---|---|---|---|
| 5,413,577 A | * | 5/1995 | Pollock | A61B 17/1735 29/897 |
| 6,752,364 B1 | * | 6/2004 | Lim | A47C 19/005 248/188.6 |
| 8,439,956 B2 | * | 5/2013 | Ko | A61B 17/8061 606/281 |
| 2003/0100898 A1 | * | 5/2003 | Wellisz | A61B 17/688 606/297 |
| 2006/0089648 A1 | * | 4/2006 | Masini | A61B 17/1615 606/71 |
| 2006/0142767 A1 | * | 6/2006 | Green | A61B 17/80 606/71 |
| 2007/0185489 A1 | * | 8/2007 | Abdou | A61B 17/7059 606/255 |
| 2007/0293865 A1 | * | 12/2007 | Ko | A61B 17/688 606/916 |
| 2008/0200954 A1 | * | 8/2008 | Tucci | A61B 17/688 606/280 |
| 2010/0004652 A1 | * | 1/2010 | Green | A61B 17/80 606/70 |
| 2012/0203284 A1 | * | 8/2012 | Khanna | A61B 17/688 606/286 |
| 2012/0271352 A1 | * | 10/2012 | Schulze | A61B 17/562 606/247 |
| 2013/0053900 A1 | * | 2/2013 | Qwarnstrom | A61F 2/2875 606/286 |
| 2013/0060288 A1 | * | 3/2013 | Rodgers | A61B 17/1604 606/281 |

OTHER PUBLICATIONS

"International Application Serial No. PCT/US2014/035321, Written Opinion dated Oct. 27, 2014", 7 pgs.

"International Application Serial No. PCT/US2014/035321, International Preliminary Report on Patentability dated Nov. 5, 2015", 9 pgs.

* cited by examiner

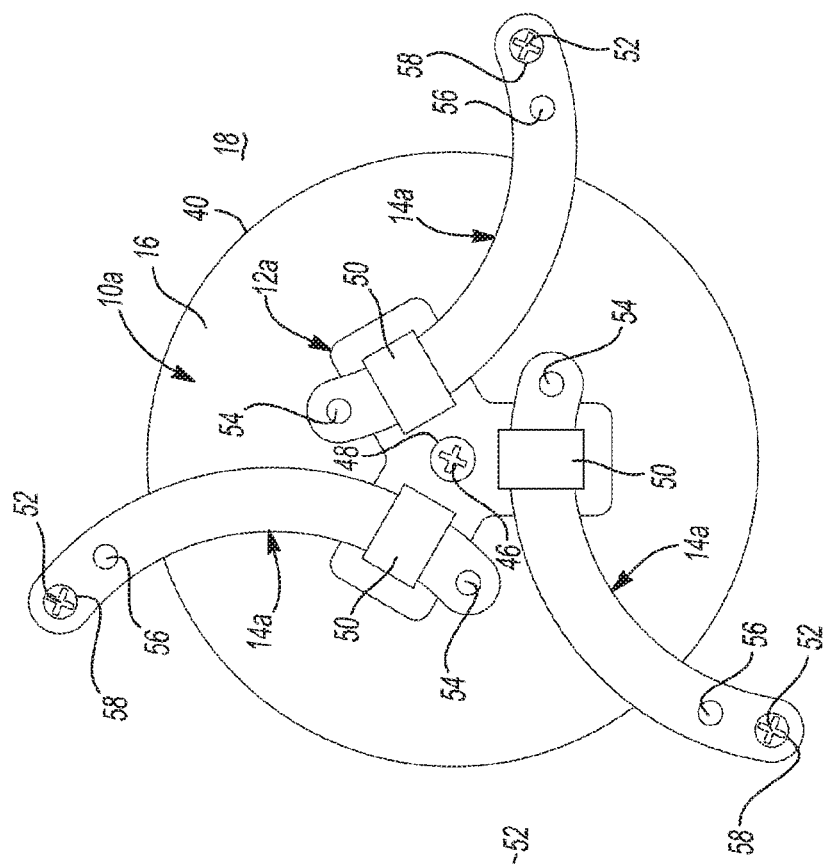
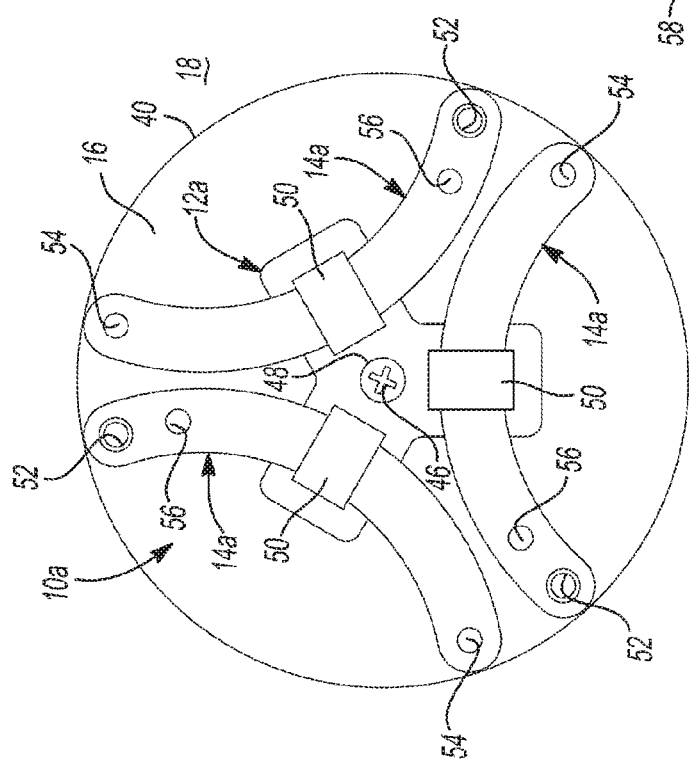

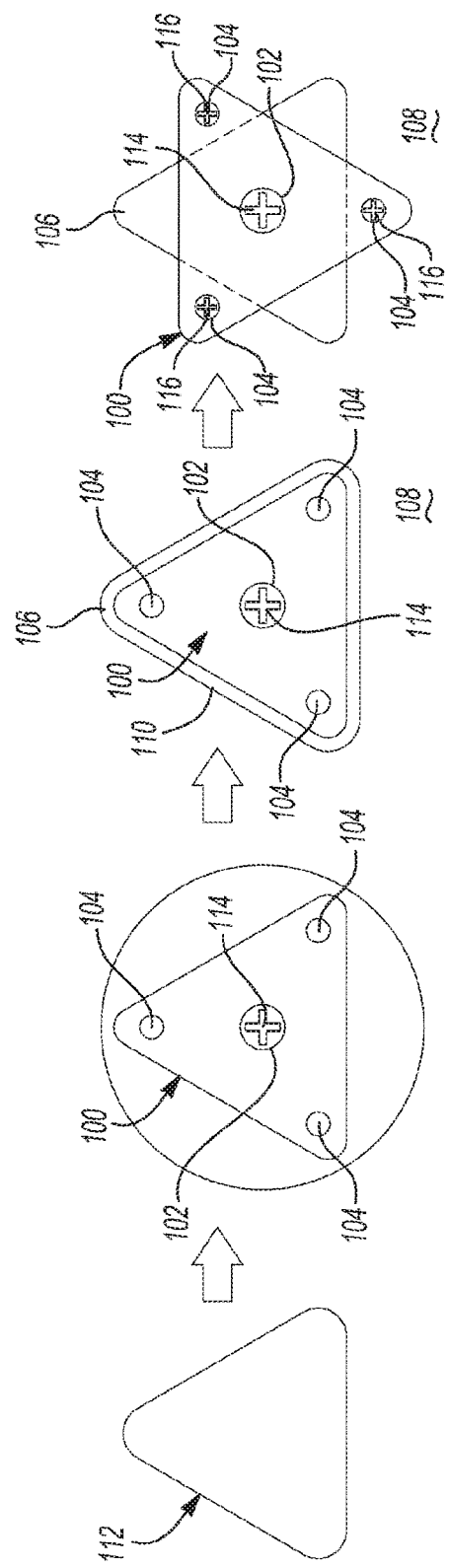

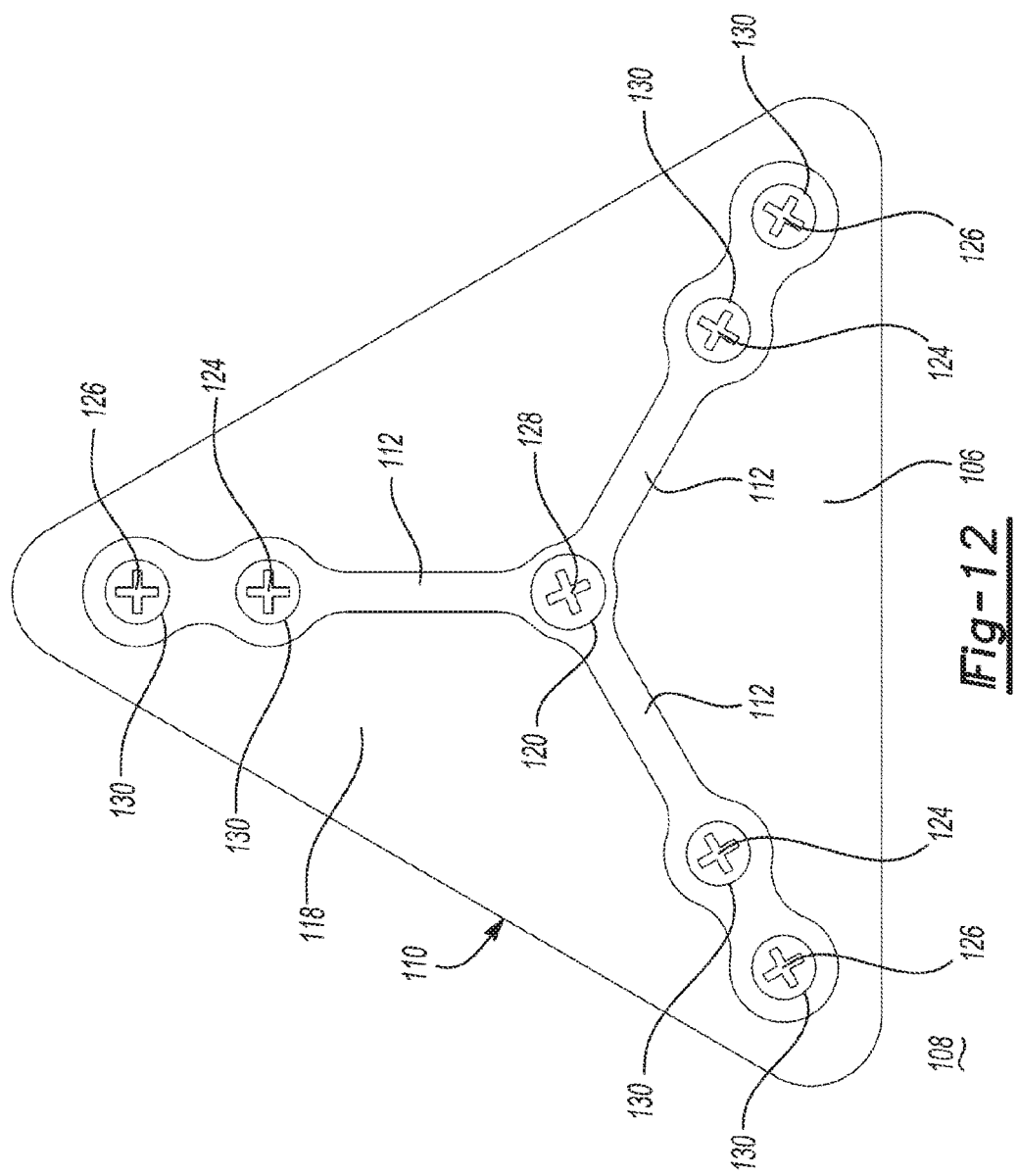

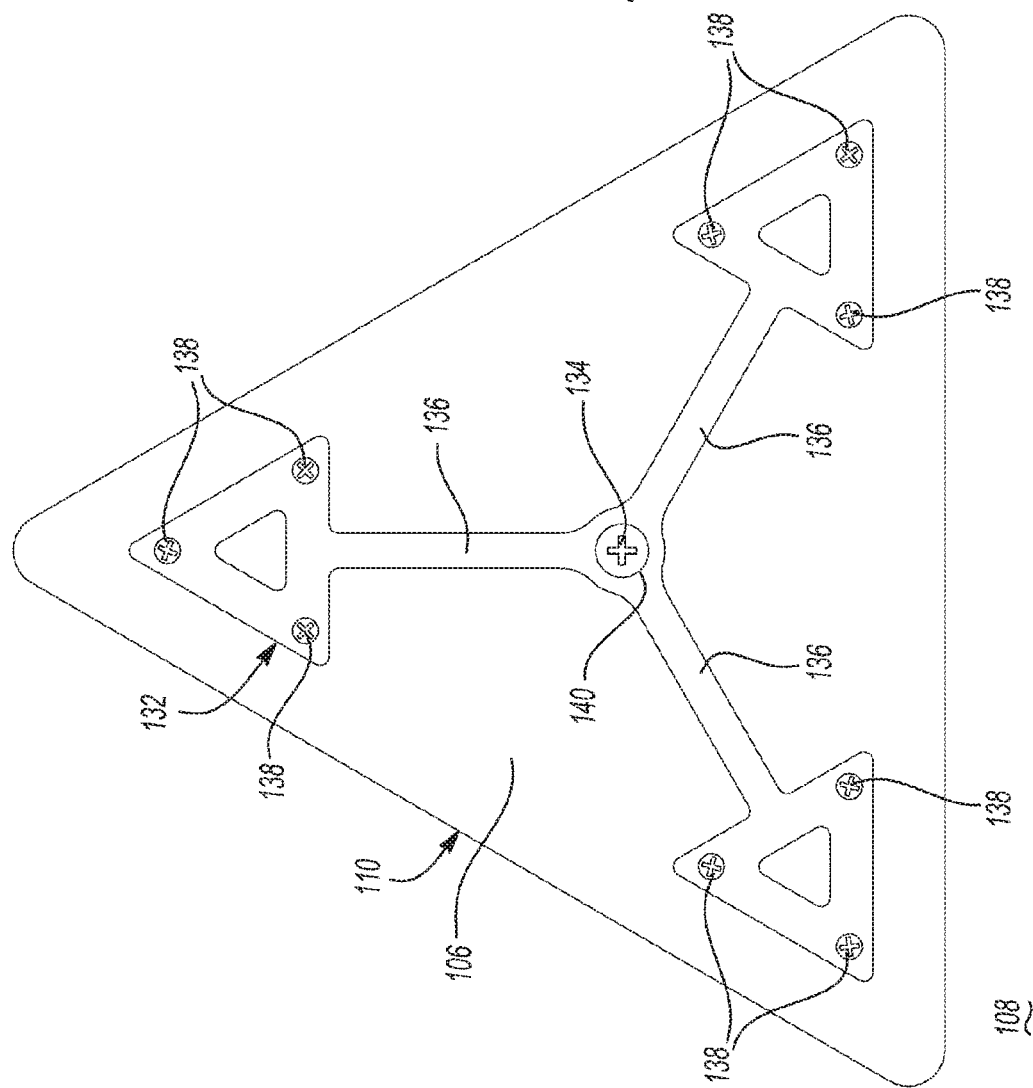

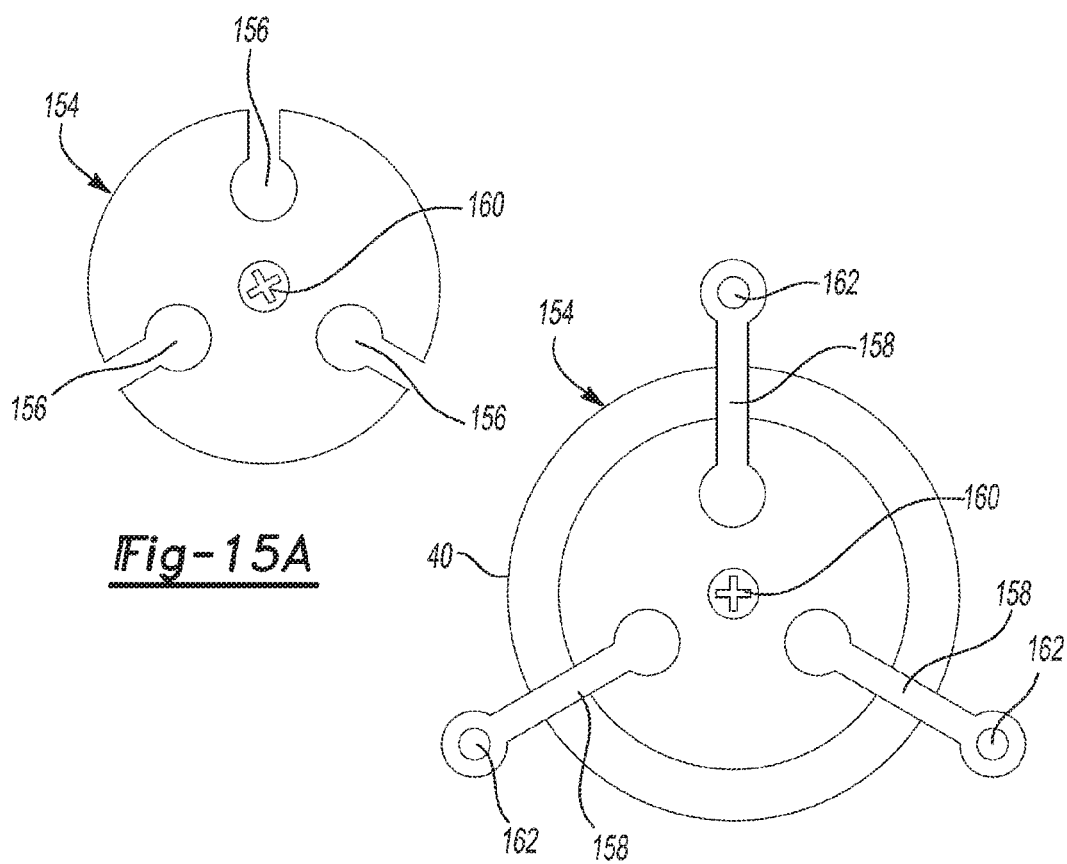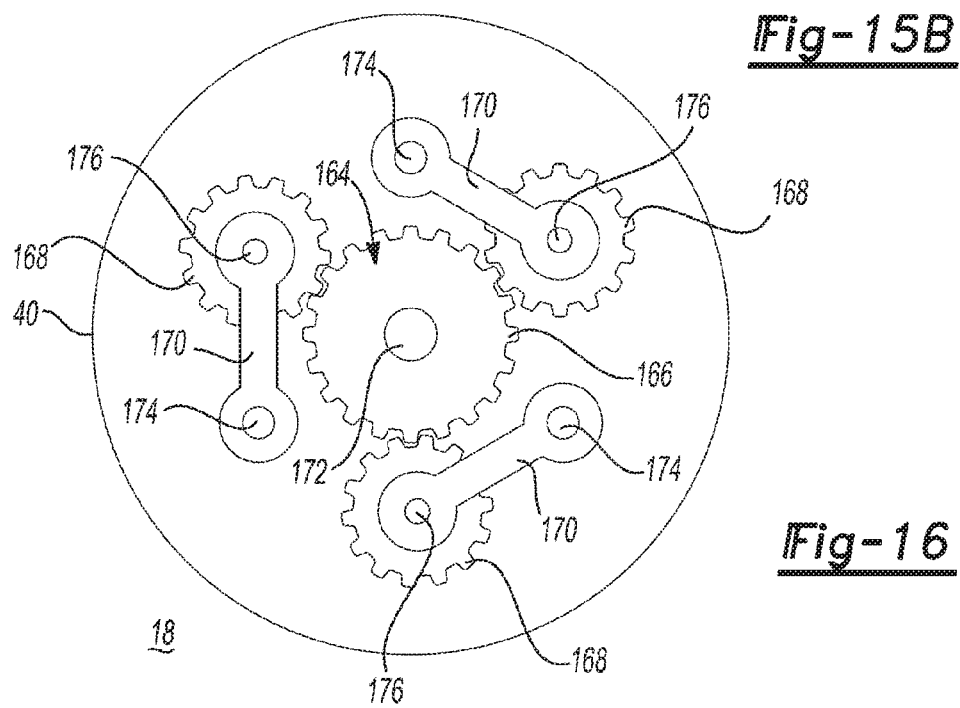

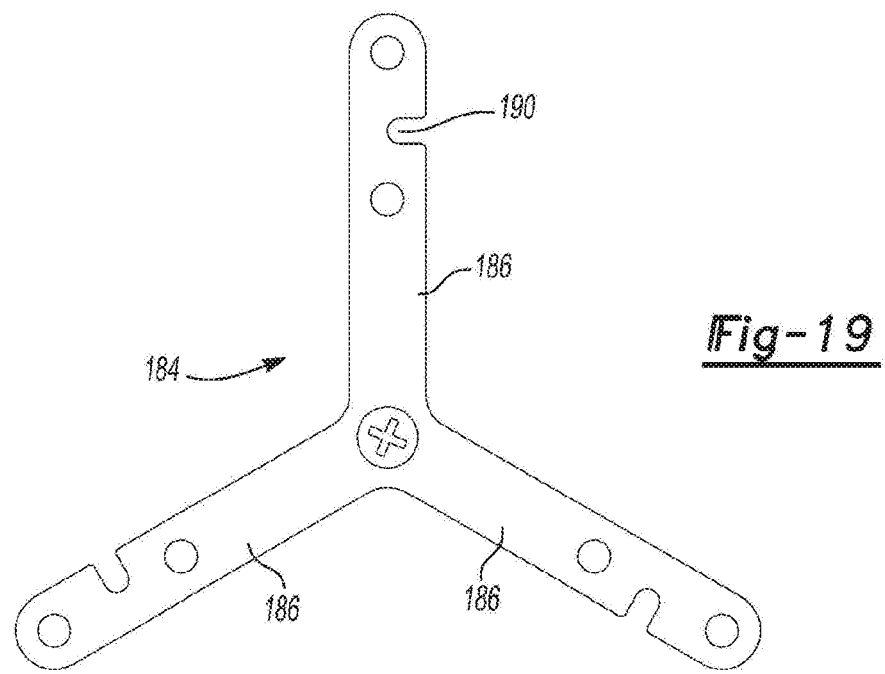
Fig-19
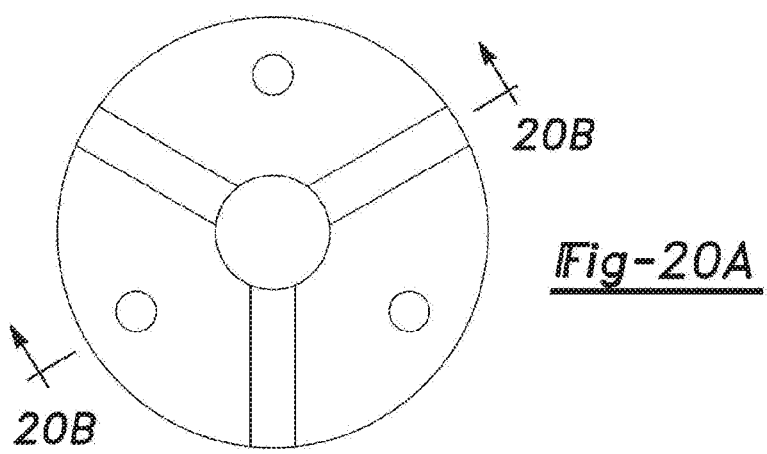
Fig-20A
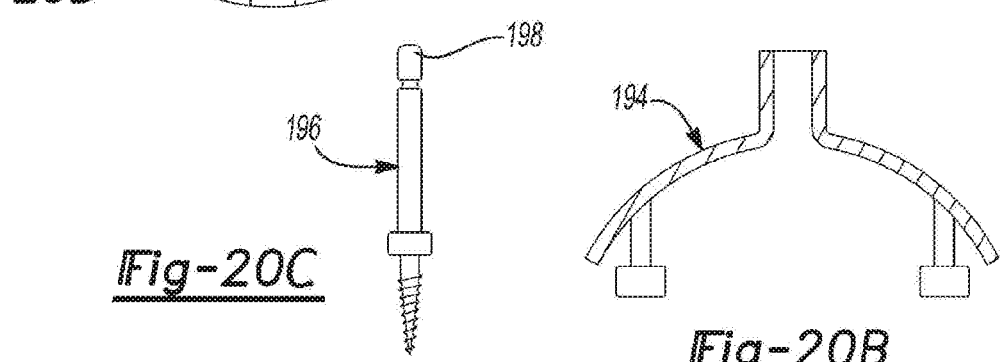
Fig-20C
Fig-20B

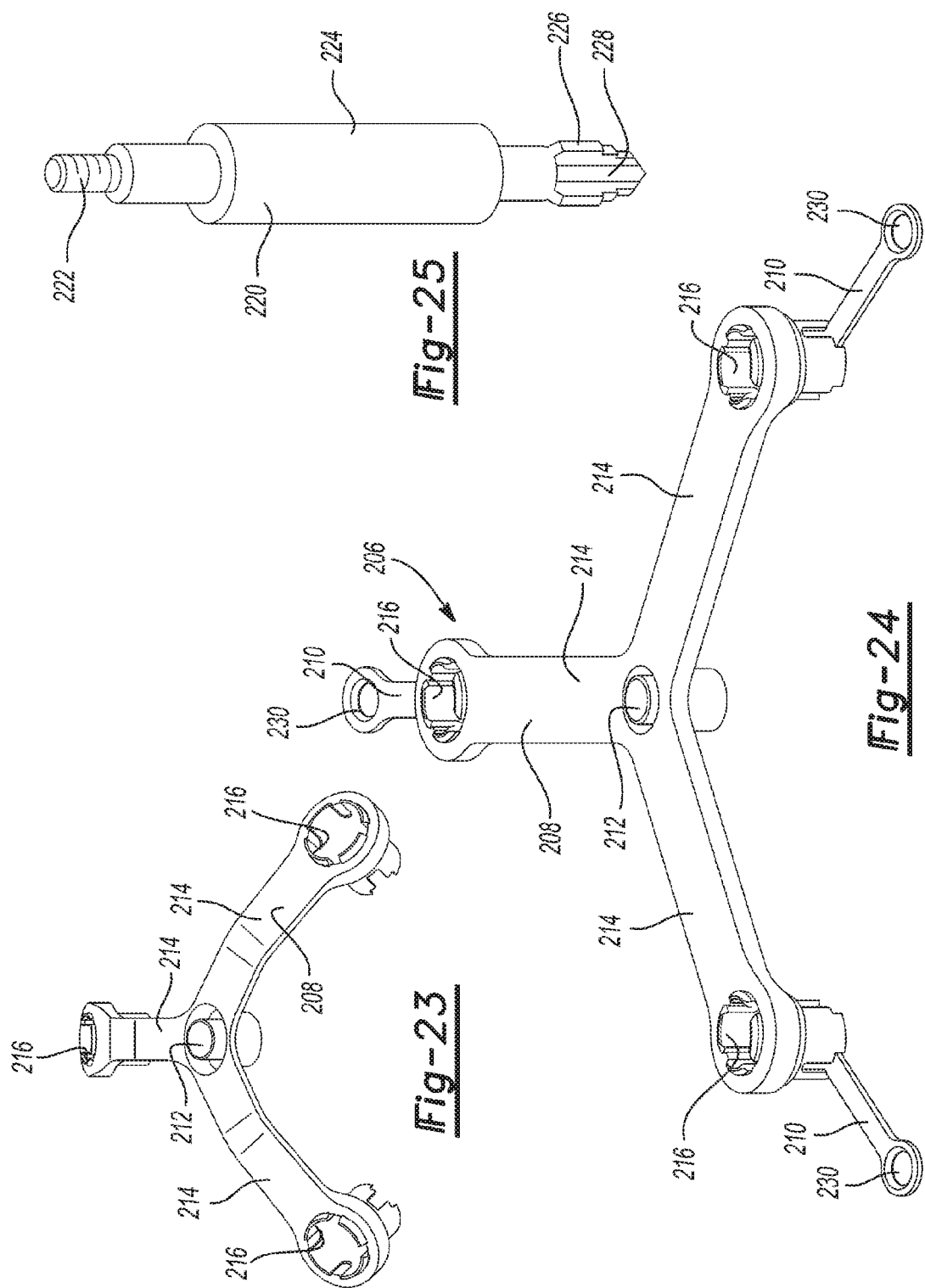

RETRACTABLE BURR HOLE PLATE AND METHOD

This application is a U.S. National Stage Application under 35 U.S.C. 371 from International Application Serial No. PCT/US2014/035321, filed on Apr. 24, 2014, and published as WO 2014/176437 A2 on Oct. 30, 2014, which claims priority to U.S. Provisional Application No. 61/816,086, filed on Apr. 25, 2013, the benefit of priority of each of which is claimed hereby, and each of which are incorporated by reference herein in its entirety.

FIELD

The present disclosure relates to a plate assembly and method for use during a craniotomy.

BACKGROUND

This section provides background information related to the present disclosure which is not necessarily prior art.

Craniotomies are performed to allow a surgeon to access a patient's brain during surgery. During such procedures, soft tissue is first dissected and retracted to allow access to a predetermined work region on the skull. Once the soft tissue is dissected and retracted, a craniotome is used to cut along a marked perimeter of the skull to remove a portion of the skull, thereby providing access to the patient's brain. The removed portion of the skull is typically referred to as a "bone flap" and is replaced after completion of the procedure.

The bone flap is conventionally replaced and attached to the skull via a series of small plates and screws. The plates typically include a main body that spans a cut line created by the craniotome and a pair of screw holes located at opposite ends of the plate. Each of the screw holes receives a screw to attach the bone flap to the skull at one end and to the bone flap at the other end. Once the screws are inserted into the respective holes of the plate, the plate spans the cut line and attaches the bone flap to the skull.

While conventional plates and screws adequately attach a bone flap to a skull, such plates are often difficult to manipulate and install during surgery. As a result, the time required to attach the bone flap to the skull is increased, which increases the overall cost and complexity of the procedure.

SUMMARY

This section provides a general summary of the disclosure, and is not a comprehensive disclosure of its full scope or all of its features.

A plate assembly for attaching a bone flap to a skull is provided and may include a first plate member attached to the bone flap and a second plate member supported by the first plate member and movable between a retracted position and an extended position relative to the first plate member. The second plate member may be removed from a cut line between the bone flap and the skull in the retracted position and may extend over the cut line in the extended position.

In another configuration, an implant system is provided and may include a first plate member having an attachment feature and a second plate member supported by the first plate member and moveable between an extended position extending over a cut line separating a first bone member and a second bone member and a retracted position separated from the cut line. The implant system may also include a tool having a first portion that engages the attachment feature to position the first plate member relative to the cut line and a second portion that engages the second plate member to move the second plate member between the extended position and the retracted position.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4 is a perspective view of a plate assembly in accordance with the principles of the present disclosure shown in a retracted position;

FIG. 5 is a perspective view of the plate assembly of FIG. 4 in an extended position;

FIG. 11A is a front view of a template for use in conjunction with a plate assembly in accordance with the principles of the present disclosure;

FIG. 11B is a front view of a plate assembly for use in conjunction with the template of FIG. 11A;

FIG. 11C is a front view of the plate assembly of FIG. 11B shown in conjunction with a cut line;

FIG. 11D is a front view of the plate assembly of FIG. 11B shown in a rotated and installed position;

FIG. 12 is a front view of a plate assembly in accordance with the principles of the present disclosure;

FIG. 13 is a front view of a plate assembly in accordance with the principles of the present disclosure;

FIG. 15A is a front view of a plate assembly in accordance with the principles of the present disclosure;

FIG. 15B is a front view of the plate assembly of FIG. 15A shown in an installed position;

FIG. 16 is a front view of a plate assembly in accordance with the principles of the present disclosure;

FIG. 19 is a front view of a plate assembly in accordance with the principles of the present disclosure;

FIG. 20A is a top view of a stencil for use in conjunction with a plate member in accordance with the principles of the present disclosure;

FIG. 20B is a cross-sectional view of the stencil of FIG. 20A, taken through the line 20B-20B;

FIG. 20C is a side view of a fastener for use in conjunction with the stencil of FIG. 20A;

FIG. 23 is a perspective view of a plate assembly in accordance with the principles of the present disclosure;

FIG. 24 is a perspective view of the plate assembly of FIG. 23 incorporating a series of movable plates;

FIG. 25 is a perspective view of a tool for use in installing the plate assembly of FIGS. 23 and 24;

Corresponding reference numerals indicate corresponding parts throughout the several views of the drawings.

DETAILED DESCRIPTION

Figure 1:
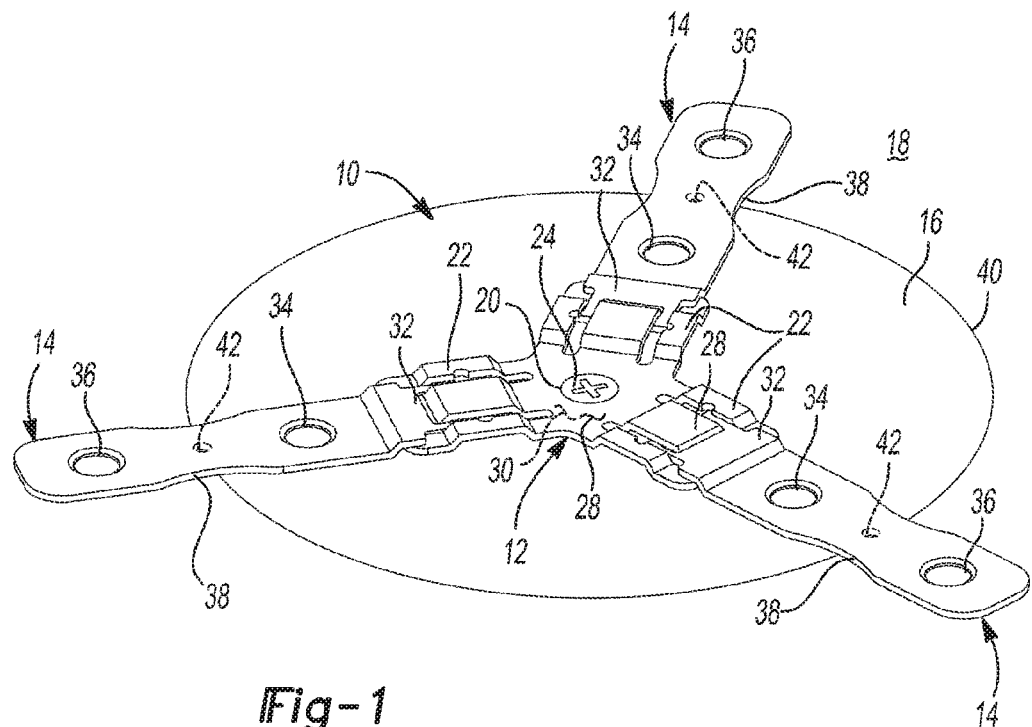
FIG. 1 is a perspective view of a plate assembly in accordance with the principles of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 2:
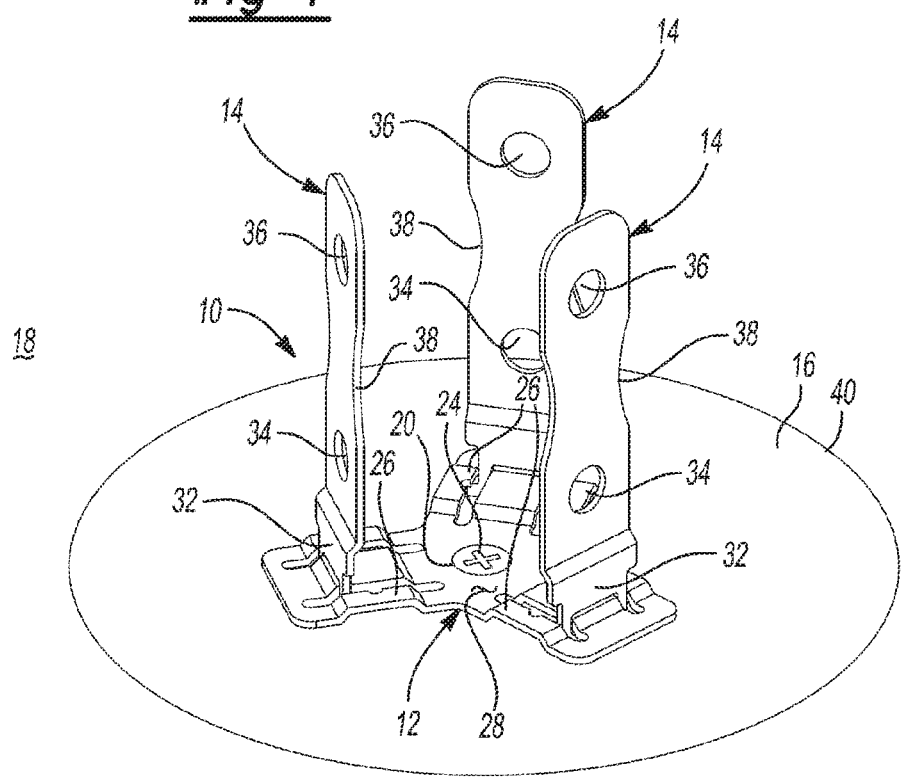
FIG. 2 is a perspective view of the plate assembly of FIG. 1 in a retracted position.
Figure 3:
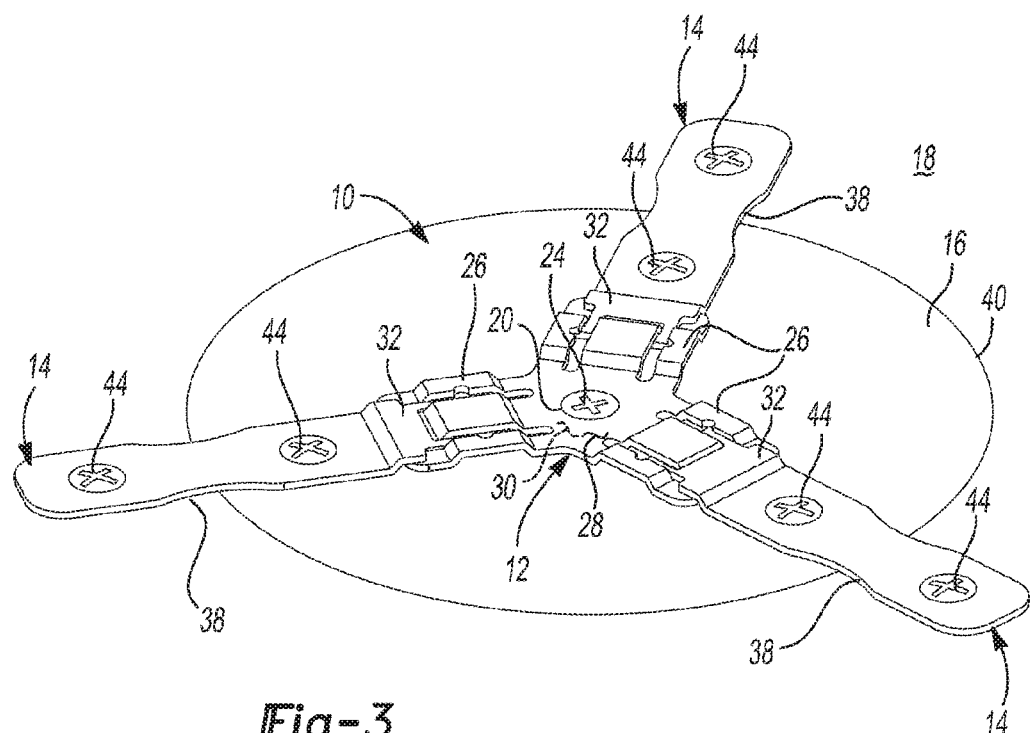
FIG. 3 is a perspective view of the plate assembly of FIG. 1 in an extended and installed position.

With reference to FIGS. 1-3, a plate assembly 10 for use during a craniotomy is provided and may include a main plate 12 and a series of attachment plates 14 attached to the main plate 12. The main plate 12 and the attachment plates 14 may be used during a craniotomy to aid in removal of a bone flap 16 from a skull 18 and, subsequently, to reattach the bone flap 16 to the skull 18 following a surgical procedure. While the plate assembly 10 will be described and shown in conjunction with a craniotomy, the plate assembly 10 may be used during any surgical procedure to reattach a portion of a removed bone within any location of a body.

The main plate 12 may include an attachment aperture 20 and a series of arms 22 radiating from the attachment aperture 20. The attachment aperture 20 may be formed through the main plate 12 and may be centrally located on the main plate 12. The attachment aperture 20 may receive a fastener 24 to attach the main plate 12 to the bone flap 16.

The arms 22 may extend generally from the main body 12 and may each include a tab 26. The tab 26 may extend from a surface 28 formed on an opposite side of the main plate 12 from a bone-engaging surface 30. The tabs 26 may provide an attachment location for attaching each of the attachment plates 14 to the main plate 12.

The attachment plates 14 may be connected to the main plate 12 at the tabs 26 and may be movable from a retracted position (FIG. 2) to an extended position (FIGS. 1 and 3). The attachment plates 14 may each include a hinge 32, a first attachment aperture 34, a second attachment aperture 36, and a reduced-width portion 38. The hinge 32 may be attached to the tab 26 such that a portion of the hinge 32 is captivated in place under the tab 26. Attachment of the hinge 32 to the tab 26 allows the attachment plates 14 to be moved between the retracted position and the extended position.

The first attachment aperture 34 may be disposed proximate to the hinge 32 and may be positioned at a location over the bone flap 16 to allow the attachment plate 14 to be attached to the bone flap 16 at the first attachment aperture 34. The second attachment aperture 36 may be positioned along a length of the attachment plates 14 such that the second attachment aperture 36 is positioned over the skull 18 when the attachment plates 14 are in the extended position. Accordingly, when fasteners are respectively inserted into the second attachment aperture 36 of the attachment plates 14, the attachment plates 14 may be attached to the skull 18 at the second attachment aperture 36.

The reduced-width portion 38 may be disposed along a length of the attachment plates 14 generally between the first attachment aperture 34 and the second attachment aperture 36. The reduced-width portion 38 may be positioned between the first attachment aperture 34 and the second attachment aperture 36 such that the reduced-width portion 38 is located over a cut line 40 that separates the bone flap 16 from the skull 18. The reduced-width portion 38 may include an aperture 42 formed therethrough that may be used by a surgeon during installation of the plate assembly 10 to mark and/or score the cut line 40 on the skull 18.

With continued reference to FIGS. 1-3, operation of the plate assembly 10 will be described in detail. The plate assembly 10 may be installed on the skull 18 at any desired location. The plate assembly 10 may first be installed by locating the main plate 12 at a desired location on the skull 18 and subsequently inserting the fastener 24 into the attachment aperture 20 of the main plate 12. Attaching the main plate 12 to the skull 18 may allow for movement of the main plate 12 relative to the skull 18 to allow the main plate 12 to rotate relative to the skull 18 about the fastener 24. Once the main plate 12 is attached to the skull 18 via the fastener 24, the attachment plate 14 may be moved into the extended position (FIGS. 1 and 3) and a pencil or other marking/scoring device (none shown) may be inserted into one or more of the apertures 42 of the attachment plates 14 to mark the cut line 40 on the skull 18. Once the pencil or other scoring device is received within the aperture 42 and is in contact with the skull 18 below one or more of the attachment plates 14, a force may be applied to the main plate 12 to rotate the main plate 12 about the fastener 24. The main plate 12 may be rotated three hundred and sixty degrees (360°) to allow the pencil or other scoring device to identify the cut line 40 on the skull 18.

The attachment plates 14 may be moved from the extended position (FIGS. 1 and 3) to the retracted position (FIG. 2) once the cut line 40 is formed on the skull 18. At this point, a craniotomy process may be performed to separate the bone flap 16 from the skull 18. Specifically, a craniotome or other saw may be used to cut the skull 18 along the cut line 40 to separate the bone flap 16 from the skull 18. Once separated, the plate assembly 10 may be used to grip and subsequently remove the bone flap 16 from the skull 18. Namely, a surgeon may grab one or more of the attachment plates 14 to apply a force on the bone flap 16 via the attachment plates 14 and main plate 12 to remove the bone flap 16 from the skull 18. When the bone flap 16 is removed from the skull 18, the plate assembly 10 remains attached to the bone flap 16. In one configuration, the fastener 24 may be driven further into the bone flap 16 following formation of the cut line 40 to restrict relative rotation between the main plate 12 and the bone flap 16. Accordingly, a position of the main plate 12 and, thus, the attachment plates 14 relative to the bone flap 16, is maintained when the bone flap 16 is removed from the skull 18.

After completion of the surgical procedure, the bone flap 16 is reattached to the skull 18 via the plate assembly 10. Specifically, the plate assembly 10 may be used to provide a grip to allow the surgeon to easily hold the bone flap 16 when re-installing the bone flap 16 on the skull 18. For example, the surgeon may grab the bone flap 16 via one or more of the attachment plates 14 when the attachment plates 14 are in the retracted position. The surgeon may position the bone flap 16 relative to the skull 18 by holding the attachment plates 14. Once the position of the bone flap 16 relative to the skull 18 is achieved, a force may be applied to the attachment plates 14 to rotate the attachment plates 14 from the retracted position to the extended position.

Rotation of the attachment plates 14 from the retracted position to the extended position causes the first attachment aperture 34 of each attachment plate 14 to oppose the bone flap 16 and, likewise, causes the second attachment apertures 36 of each attachment plate 14 to oppose the skull 18.

In this position, each of the attachment plates 14 is positioned relative to the cut line 40 such that the reduced-width portion 38 of each attachment plate 14 spans the cut line 40. Fasteners 44 may be respectively inserted into the first attachment apertures 34 and the second attachment apertures 36 of the attachment plates 14 to secure the attachment plates 14 to the bone flap 16 and the skull 18. Upon insertion of the fasteners 44 into the first aperture 34, the second aperture 36, the bone flap 16, and the skull 18, the bone flap 16 is reattached to the skull 18 and movement of the bone flap 16 relative to the skull 18 is restricted by the plate assembly 10. Accordingly, the plate assembly 10 maintains a position of the bone flap 16 relative to the skull 18 to allow the bone flap 16 to heal and reattach to the skull 18 over time.

With reference to FIGS. 4 and 5, another plate assembly 10a is provided and may include a main plate 12a and a series of attachment plates 14a. In view of the substantial similarity in structure and function of the components associated with the plate assembly 10 with respect to the plate assembly 10a, like reference numerals are used hereinafter and in the drawings to identify like components while like reference numerals containing letter extensions are used to identify those components that have been modified.

The plate assembly 10a may be used to remove a bone flap 16 from a skull 18 and, subsequently, may be used to reattach the bone flap 16 to the skull 18, as described above with respect to the plate assembly 10a. Namely, the main plate 12a may be attached to the bone flap 16 by inserting a fastener 46 into an aperture 48 formed through the main plate 12a. Insertion of the fastener 46 into the aperture 48 attaches the main plate 12a and, thus, the attachment plates 14, to the bone flap 16. Specifically, the main plate 12a may include a series of retention features 50 that slidably support the attachment plates 14a relative to the main plate 12a.

The attachment plates 14a may be respectively and slidably received within the retention features 50 of the main plate 12a and may be moved between a retracted position (FIG. 4) and an extended position (FIG. 5). Each attachment plate 14a may include an aperture 52, a projection 54 located at an opposite end of the attachment plate 14a than the aperture 52, and a projection 56 disposed along a length of the attachment plate 14a between the aperture 52 and the projection 54. The aperture 52 may be formed through the attachment plates 14a while the projections 54, 56 may be partially formed into the attachment plates 14a such that a depression is formed on an opposite side of each attachment plate 14a than the projections 54, 56.

With continued reference to FIGS. 4 and 5, operation of the plate assembly 10a will be described in detail. The plate assembly 10a may be attached to the bone flap 16 in the retracted position (FIG. 4). In this position, each of the attachment plates 14 are positioned relative to and within the retention features 50 of the main plate 12a such that the retention features 50 are located between the projections 54, 56. Once the surgeon separates the bone flap 16 from the skull 18 at the cut line 40, the plate assembly 10a and bone flap 16 may be removed from the skull 18 to allow the surgeon access to the patient's brain.

Upon completion of the procedure, the surgeon may reinstall the bone flap 16 by first inserting the bone flap 16 into the skull 18. Once inserted, a force may be applied to the attachment plates 14a to move the attachment plates 14a from the retracted position (FIG. 4) to the extended position (FIG. 5). Specifically, the attachment plates 14a may be translated relative to and within the retention features 50 until the projections 56 of each attachment plate 14a contact the retention features 50. At this point, each attachment plate 14a is in a fully extended state such that the aperture 52 of each attachment plate 14a extends over the skull 18.

A fastener 58 may be inserted into each aperture 52 of the attachment plates 14a to secure the attachment plates 14a to the skull 18. Securing the attachment plates 14a to the skull 18 via the fasteners 58 likewise secures the main plate 12a and bone flap 16, as the attachment plates 14a are attached to the main plate 12a via interaction between the attachment plates 14a and the retention features 50. As with the plate assembly 10, the plate assembly 10a serves to maintain a relative position of the bone flap 16 and the skull 18 to allow the bone flap 16 to heal.

Figure 6:
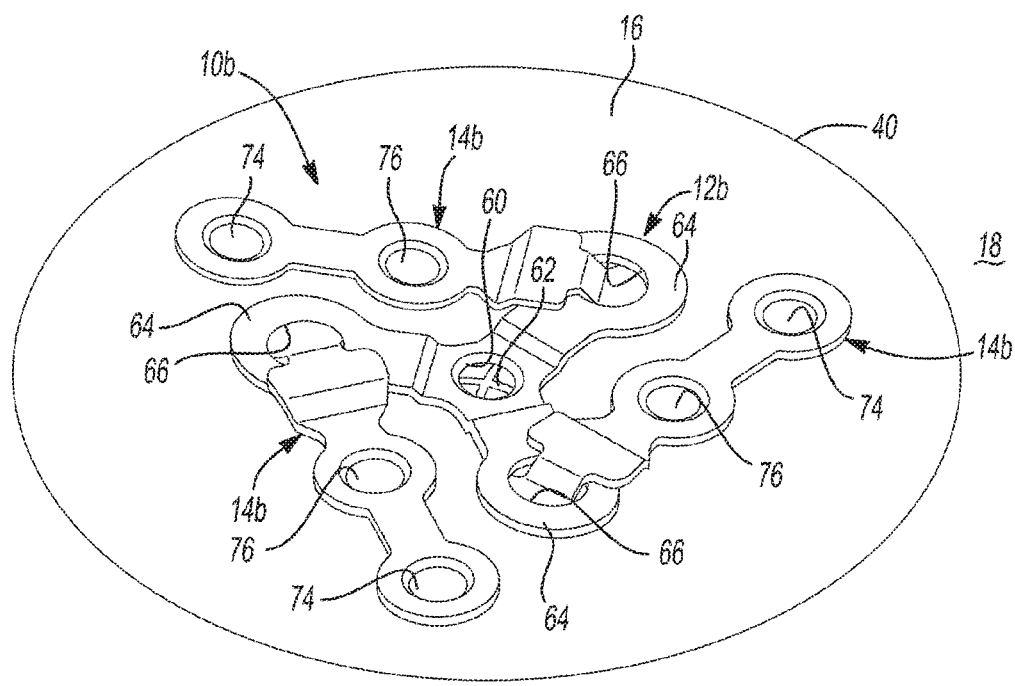
FIG. 6 is a perspective view of a plate assembly in accordance with the principles of the present disclosure shown in a retracted position.
Figure 7:
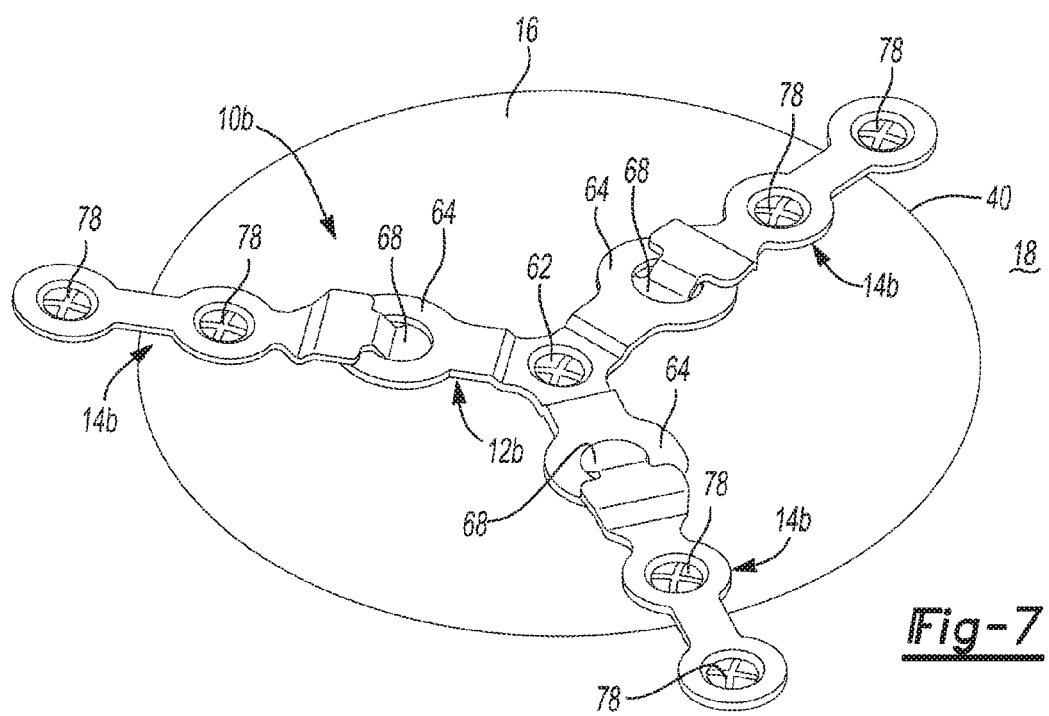
FIG. 7 is a perspective view of the plate assembly of FIG. 6 in an extended position.
Figure 8:
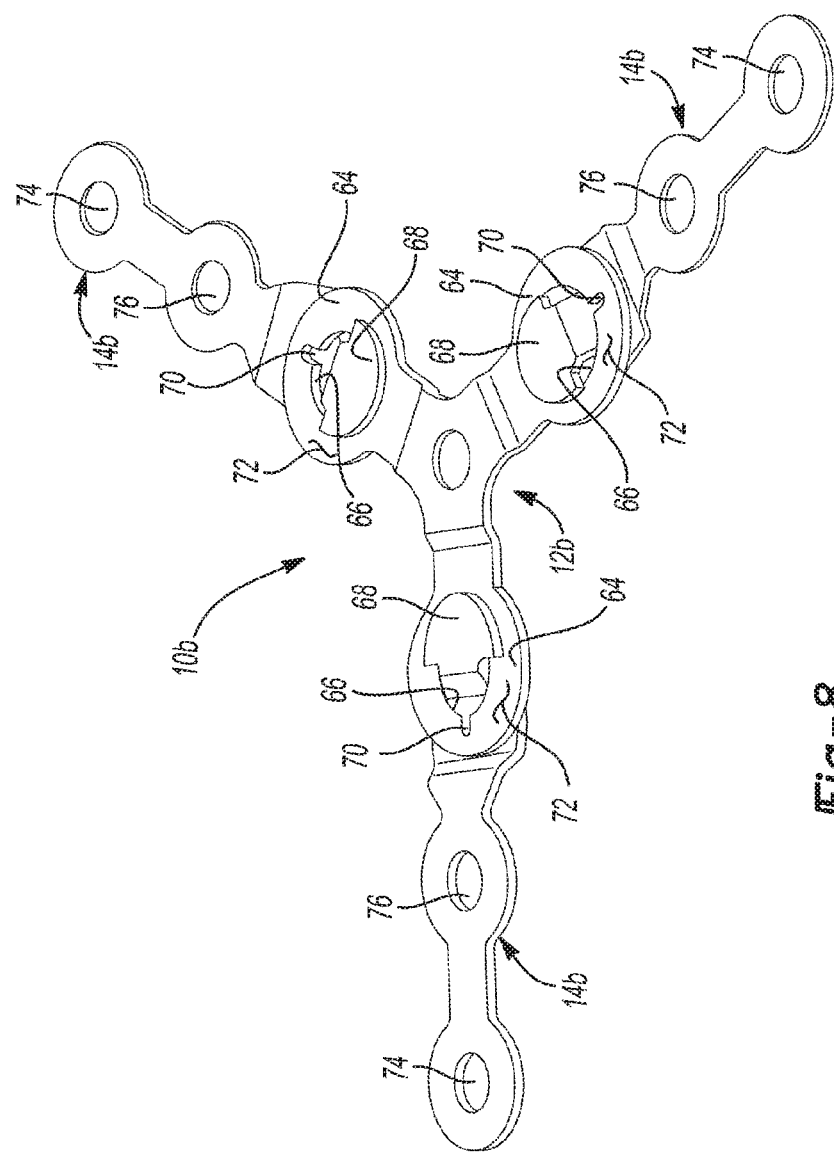
FIG. 8 is a perspective view of the plate assembly of FIG. 6 in an extended position.

With particular reference to FIGS. 6-8, a plate assembly 10b is provided and may include a main plate 12b and a series of attachment plates 14b. In view of the substantial similarity in structure and function of the components associated with the plate assembly 10 with respect to the plate assembly 10b, like reference numerals are used hereinafter and in the drawings to identify like components while like reference numerals containing letter extensions are used to identify those components that have been modified.

The plate assembly 10b may be used during removal of a bone flap 16 from a skull 18. Further, the plate assembly 10b may be used to reattach the bone flap 16 to the skull 18 following a surgical procedure.

The main plate 12b may include an aperture 60 formed through a center of the main plate 12b. The aperture 60 may receive a fastener 62 to attach the main plate 12b to the bone flap 16. The main plate 12b may additionally include a series of arms that radiate from the aperture 60, as well as a series of apertures 66 respectively associated with each of the arms 64.

The attachment plates 14b may each include a projection 68 received by respective ones of the apertures 66 to connect the attachment plates 14b to the main plate 12b. Specifically, the projection 68 may be inserted into each aperture via a slot 70 (FIG. 8) that allows the projection 68 to be inserted into the aperture 66. Once the projection 68 is received into the aperture 66, the attachment plates 14b may be rotated approximately ninety degrees (90°) to allow the projection 68 of each attachment plate 14b to be captured by and engage a bottom surface 72 (FIG. 8) of each arm 64. Engagement between the projection 68 of each attachment plate 14b and the bottom surface 72 of each arm 64 connects each attachment plate 14b to the main plate 12b while concurrently allowing each attachment plate 14b to pivot about an axis extending substantially perpendicular to the bottom surface 72. Namely, engagement between each projection 68 and the bottom surface 72 of each arm 64 maintains engagement between each attachment plate 14b and the main plate 12b while concurrently allowing the attachment plates 14b to pivot relative to the main plate 12b between the retracted position (FIG. 6) and the extended position (FIGS. 7 and 8).

Each attachment plate 14b may include an aperture 74 located proximate to a distal end of each attachment plate 14b and an aperture 76 located between the aperture 74 and the projection 68. When the attachment plates 14b are in the retracted position, each of the apertures 74, 76 are located above the bone flap 16. Conversely, when the attachment plates 14b are moved into the extended position, the aperture 74 opposes the skull 18 while the aperture 76 opposes the bone flap 16.

With continued reference to FIGS. 6-8, operation of the plate assembly 10b will be described in detail. The main plate 12b may be attached to the bone flap 16 via the fastener 62 to fix the main plate 12b for movement with the bone flap 16. At this point, the attachment plates 14b may be in the retracted position (FIG. 6) to allow the cut line 40 to be made between the bone flap 16 and the skull 18. Once the bone flap 16 is separated from the skull 18, the bone flap 16 may be removed from the skull 18 along with the plate assembly 10b.

Following the surgical procedure, a surgeon may reposition the bone flap 16 in the skull 18 and may exert a force on each attachment plate 14b to move the attachment plates 14b from the retracted position to the extended position. Namely, a rotational force may be applied to each attachment plate 14b to rotate or pivot each attachment plate 14b at the projection 68 of each attachment plate 14b. When the attachment plates 14b are moved into the extended position, the aperture 74 is positioned such that the aperture 74 opposes the skull 18 while the aperture 76 opposes the bone flap 16. At this point, a fastener 78 may be inserted into the aperture 76 to connect the attachment plates 14b to the bone flap 16 and another fastener 78 may be inserted into the aperture 74 to connect the attachment plates 14b to the skull 18. Connecting the attachment plates 14 to the bone flap 16 and the skull 18 via the fasteners 78 and apertures 74, 76 allows the attachment plates 14b to span the cut line 40 and, further, restricts relative movement between the attachment plates 14b, the bone flap 16, and the skull 18. Accordingly, the plate assembly 10b maintains the relative position of the bone flap 16 and the skull 18 to allow the bone flap 16 to heal following surgery.

Figure 9:
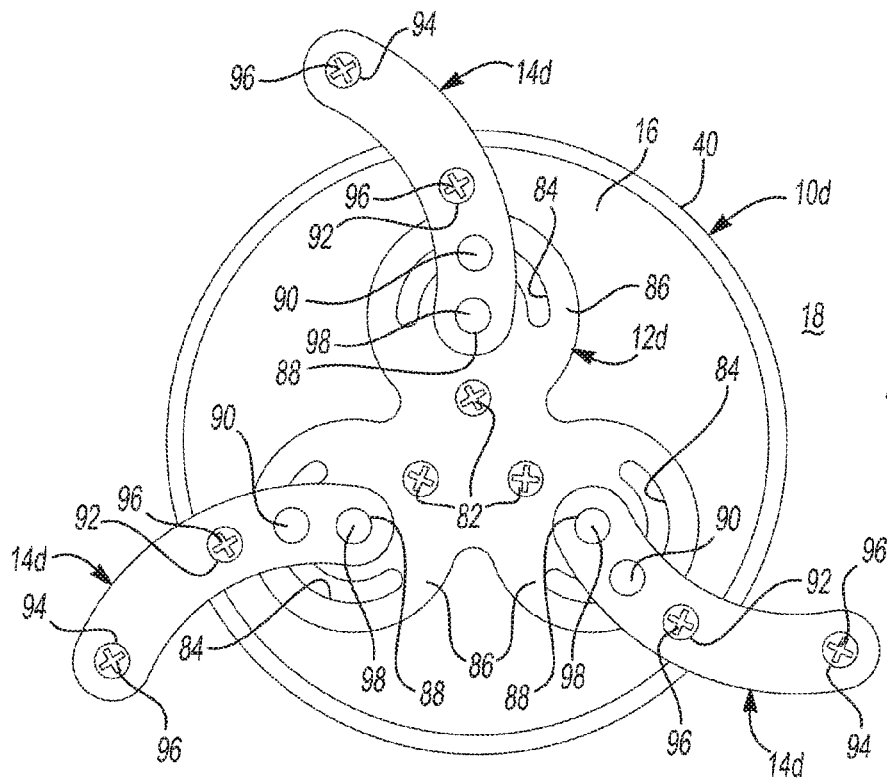
FIG. 9 is a perspective view of a plate assembly in accordance with the principles of the present disclosure shown in a retracted position.
Figure 10:
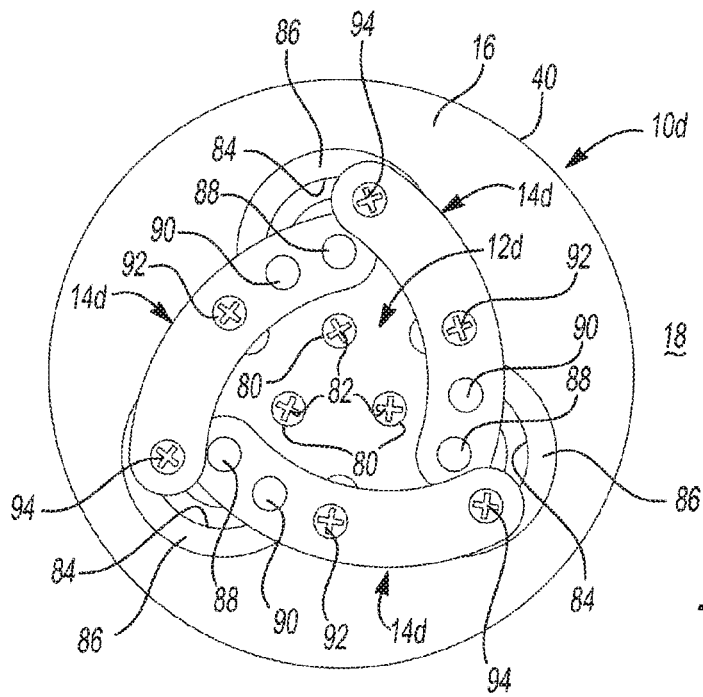
FIG. 10 is a perspective view of the plate assembly of FIG. 9 in an extended position.

With particular reference to FIGS. 9 and 10, a plate assembly 10d is provided and may include a main plate 12d and a series of attachment plates 14d. In view of the substantial similarity in structure and function of the components associated with the plate assembly 10 with respect to the plate assembly 10d, like reference numerals are used hereinafter and in the drawings to identify like components while like reference numerals containing letter extensions are used to identify those components that have been modified.

The main plate 12d may include a series of apertures 80 that respectively receive fasteners 82 to secure the main plate 12d to a bone flap 16. The main plate 12d may additionally include a series of slots 84, each having a substantially arcuate shape and each respectively formed in an arm 86 of the main plate 12d.

The attachment plates 14d may be pivotably attached to the main plate 12d and may each include a pivot aperture 88, a projection 90, and a pair of attachment apertures 92, 94. The attachment plates 14d may have a substantially arcuate shape, such that the ends of the attachment plates 14d are disposed within the perimeter of the arms 86 when the attachment plates are in the retracted position (FIG. 9). As will be described in greater detail below, the attachment apertures 92, 94 may respectively receive fasteners 96 to secure the attachment plates 14d to the bone flap 16 and to the skull 18 when the attachment plates 14d are moved relative to the main plate 12d from the retracted position (FIG. 9) to the extended position (FIG. 10).

The attachment plates 14d may be attached to the main plate 12d via the pivot aperture 88. Namely, a rivet 98 (FIG. 10) may be inserted into each pivot aperture 88 to pivotably couple the attachment plates 14d to the main plate 12d. The attachment plates 14d may additionally be attached to the main plate 12d via the projection 90, which may extend into and be slidably received by the slots 84 of each arm 86. Cooperation between the projections 90 and the respective slots 84 may guide movement of the attachment plates 14d relative to the main plate 12d, as the attachment plates 14 are pivoted about the rivet 18 between the retracted position and the extended position.

With continued reference to FIGS. 9 and 10, operation of the plate assembly 10d will be described in detail. The plate assembly 10d may be positioned on the skull 18 prior to separation of the bone flap 16 from the skull 18. The attachment plates 14d may be moved into the extended position (FIG. 10) from the retracted position (FIG. 9) to mark a location of each attachment aperture 94 on the skull 18 and, likewise, to mark a location of each attachment aperture 92 on the skull 18 within a boundary of the bone flap 16 defined by the cut line 40. Once the marks are made on the skull 18, the attachment plates 14d may be moved into the retracted position and the fasteners 82 may be used to secure the main plate 12d to the bone flap 16 prior to separating the bone flap 16 from the skull 18 at the cut line 40. Alternatively, the bone flap 16 may be separated from the skull 18 at the cut line 40 prior to attaching the main plate 12d to the bone flap 16 via the fasteners 82. Regardless of whether the main plate 12d is attached to the bone flap 16 prior to or following separation of the bone flap 16 from the skull 18, the bone flap 16 may be removed from the skull 18 to allow access to a patient's brain.

Once a surgical procedure is performed on the patient's brain, the bone flap 16 may be reattached to the skull 18 via the plate assembly 10d. Specifically, the bone flap 16 may be positioned on the skull 18 with the plate assembly 10d initially in the retracted position. A force may be applied to the attachment plates 14d to pivot the attachment plates 14d about the rivet 98 to allow the attachment plates 14d to move from the retracted position to the extended position.

Movement of the attachment plates 14d from the retracted position to the extended position is guided by interaction between the projection 90 of each attachment plate 14d and the slots 84 of each arm 86. Once the attachment plates 14d are moved into the extended position (FIG. 10), the fasteners 96 may be respectively inserted into the attachment apertures 92 to secure the attachment plates 14d to the bone flap 16. Likewise, the fasteners 96 may be inserted into the attachment apertures 94 to secure a position of the attachment plates 14d relative to the skull 18. Securing the position of the attachment plates 14d to the bone flap 16 and to the skull 18 likewise secures a position of the bone flap 16 relative to the skull 18, as each of the attachment plates 14d spans the cut line 40 when the attachment plates 14d are in the extended state. As with the plate assembly 10, securing a position of the bone flap 16 relative to the skull 18 allows the bone flap 16 to heal following the surgical procedure.

The foregoing plate assemblies 10, 10a, 10b, 10c, 10d, each incorporate a main plate 12, 12a, 12b, 12c, 12d, respectively, and a series of attachment plates 14, 14a, 14b, 14c, 14d, respectively, that are movable relative to the main plates 12, 12a, 12b, 12c, 12d. Such movement of the attachment plates 14, 14a, 14b, 14c, 14d, relative to the main plates 12, 12a, 12b, 12c, 12d, allows the attachment plates 14, 14a, 14b, 14c, 14d, to be moved between a retracted position and an extended position to allow the attachment plates 14, 14a, 14b, 14c, 14d, to extend over a cut line 40 that separates a bone flap 16 from a skull 18. While the foregoing plate assemblies 10, 10a, 10b, 10c, 10d, include separate attachment plates 14, 14a, 14b, 14c, 14d, and a separate main plate 12, 12a, 12b, 12c, 12d, fixing a position of a bone flap 16 relative to a skull 18 could be accomplished via a single main plate, as described below.

With particular reference to FIGS. 11A-11D, a plate 100 is provided and may include a central aperture 102 and a series of attachment apertures 104. The plate 100 may be used to secure a bone flap 106 relative to a skull 108 (FIG. 11C) when the bone flap 106 is separated from the skull 108 along a cut line 110.

The bone plate 100 may include a substantially triangular shape that is similar to the shape provided by the cut line 110. Specifically, a template 112 (FIG. 11A) may include a substantially triangular shape and may be used to define the shape of the bone flap 106. For example, the template 112 may be positioned on the skull 108 prior to separating the bone flap 106 from the skull 108. The shape of the bone flap 106 may be determined based on the shape of the template 112 by either marking or scoring the shape of the template 112 on the skull 108. The bone flap 106 may be removed from the skull 108 by cutting the skull 108 along the cut line 110.

Once the bone flap 106 is separated from the skull 108 along the cut line 110, the bone flap 106 may be removed from the skull 108 to allow a surgeon access to the patient's brain.

The plate 100 may be attached to the bone flap 106 prior to or following removal of the bone flap 106 from the skull 108 by inserting a fastener 114 into the central aperture 102 of the plate 100. Once the surgical procedure on the patient's brain is complete, the surgeon may utilize the plate 100 to once again attach the bone flap 106 to the skull 108. Specifically, the plate 100 may be rotated about the fastener 114 approximately one hundred and eighty degrees (180°) such that the plate 100 is substantially one hundred and eighty degrees (180°) out of phase relative to the triangularly shaped bone flap 106 (FIG. 11D). In this position, each of the attachment apertures 104 are no longer positioned over the bone flap 106 but, rather, are positioned over the skull 108. A series of fasteners 116 may be inserted into the attachment apertures 104 of the bone plate 100 to fix a position of the bone plate 100 relative to the skull 108. Fixing a position of the plate 100 relative to the skull 108 via the fasteners 116 likewise fixes a position of the bone flap 106 relative to the skull 108, as the plate 100 is attached to the bone flap 106 via the fastener 114. Fixing a position of the bone flap 106 relative to the skull 108 allows the bone flap 106 to heal following the surgical procedure.

While the plate 100 may include a substantially solid, triangular shape, the plate 100 could include virtually any shape that, when rotated about the fastener 114, positions one or more portions of the plate 100 opposite the skull 108. For example, the plate 100 could alternatively include a rectangular shape that does not extend over the skull 108 in a first position but when rotated approximately ninety degrees (90°) relative to the bone flap 106, extends over the skull 108. Further, while the plate 100 is described and shown as being substantially solid, the plate 100 could alternatively be formed by a series of arms, as will be described in detail below.

With reference to FIG. 12, a plate 118 is provided and may include a central aperture 120 and a series of arms 122 radiating from the central aperture 120. Each of the arms 122 may include a pair of apertures 124, 126, whereby the aperture 126 is located proximate to a distal end of each arm 122 and the aperture 124 is located between the aperture 126 and the central aperture 120.

In operation, the template 112 may be used in a similar fashion as described above with respect to the plate 100 to define the shape of the bone flap 106. The plate 118 may be secured to the bone flap 106 by inserting a fastener 128 into the central aperture 120. Once the bone flap 106 is separated from the skull 108 along the cut line 110, the bone flap 106 may be removed from the skull 108 to expose a patient's brain.

Following a procedure performed on the patient's brain, the bone flap 106 may be installed in the skull 108 by rotating the plate about the fastener 128. Specifically, when the bone flap 106 is returned to the skull 108 following the surgical procedure, the plate 118 may be rotated about the fastener 128 until one or both of the apertures 124, 126 extend over the skull 108. Once one or more of the apertures 124, 126 of the arms 122 extend over the skull 104, the fasteners 128, 130 may be respectively inserted into the apertures 124, 126 to fix a position of the plate 118 relative to the skull 118, thereby fixing a position of the bone flap 106 relative to the skull 108. While the apertures 124, 126 are described as rotating into a position such that the apertures 124, 126 oppose the skull 108, the apertures 124, 126 may be spaced apart along a length of the arms 122 such that only the aperture 126 extends over the skull 108 when the plate 118 is rotated relative to the bone flap 106. If only the aperture 126 extends over the skull 108, the aperture 124 may be positioned over the bone flap 106 such that when the fasteners 128, 130 are respectively inserted into the apertures 124, 126, the fastener 130 engages the skull 108 while the fastener 128 engages the bone flap 106. Regardless of how the apertures 124, 126 are positioned relative to the bone flap 106 and the skull 108 when the plate 118 is rotated relative to the bone flap 106, use of the fasteners 128, 130 and the plate 118 fixes a position of the bone flap 106 relative to the skull 108, thereby allowing the bone flap 106 to heal following the surgical procedure.

With particular reference to FIG. 13, a plate 132 is shown for use in conjunction with a bone flap 106 having a triangular shape. As described above with respect to the bone plates 100, 118, the bone flap 106 may have a triangular shape based on use of the template 112 in creating the cut line 110. The plate 132 is similar to the plate 118, as the plate 132 may include a central aperture 134, a series of arms 136 radiating from the central aperture 134, and apertures 138 associated with the arms 136 for fixing a position of the plate 132 relative to the skull 108 following a surgical procedure.

In operation, the plate 132 may be attached to the bone flap 106 via a fastener 140 received by the central aperture 134. The plate 132 and bone flap 106 may be removed from the skull 108 to permit access to a patient's brain. The bone flap 106 may be replaced following a procedure performed on the patient's brain by inserting the bone flap 106 into the skull 108 and subsequently rotating the plate 132 about the fastener 140. For example, a force may be applied to the plate 132 to rotate the plate 132 to approximately ninety degrees (90°) such that the plate 132 no longer extends completely over the bone flap 106.

Rotating the plate 132 about the fastener 140 approximately ninety degrees (90°) causes the arms 136 to partially extend over the skull 108. In so doing, one or more of the apertures 138 associated with the arms 136 likewise may extend over the skull 108 and may receive a fastener (not shown) to fix a position of the plate 132 relative to the skull 108.

As shown in FIG. 13, the arms 136 may each include three apertures 138 located proximate to a distal end of each arm 136. In one configuration, each of the apertures 138 extend over the skull 108 and receive a fastener to secure the arms 136 at three different locations of the skull 108. In another configuration, the plate 132 may be rotated less than ninety degrees (90°) about the central aperture 134 relative to the bone plate 106 such that only one or two of the apertures 138 extend over the skull 108 while the other aperture(s) 138 extend over the bone flap 106. Accordingly, the distal end of each arm 136 may be concurrently fixed to the bone flap 106 and the skull 108 when at least one aperture 138 extends over the skull 108 and at least one aperture 138 extends over the bone flap 106. Regardless of whether each aperture 138 extends over the skull 108, fixing the arms 136 relative to the skull 108 likewise fixes a position of the bone flap 106 relative to the skull 108, as the plate 132 is fixed for movement with the bone flap 106 via the fastener 140. Accordingly, once the plate 132 is installed, a position of the bone flap 106 relative to the skull 108 is maintained, thereby allowing the bone flap 106 to heal following the surgical procedure.

Figure 14A:
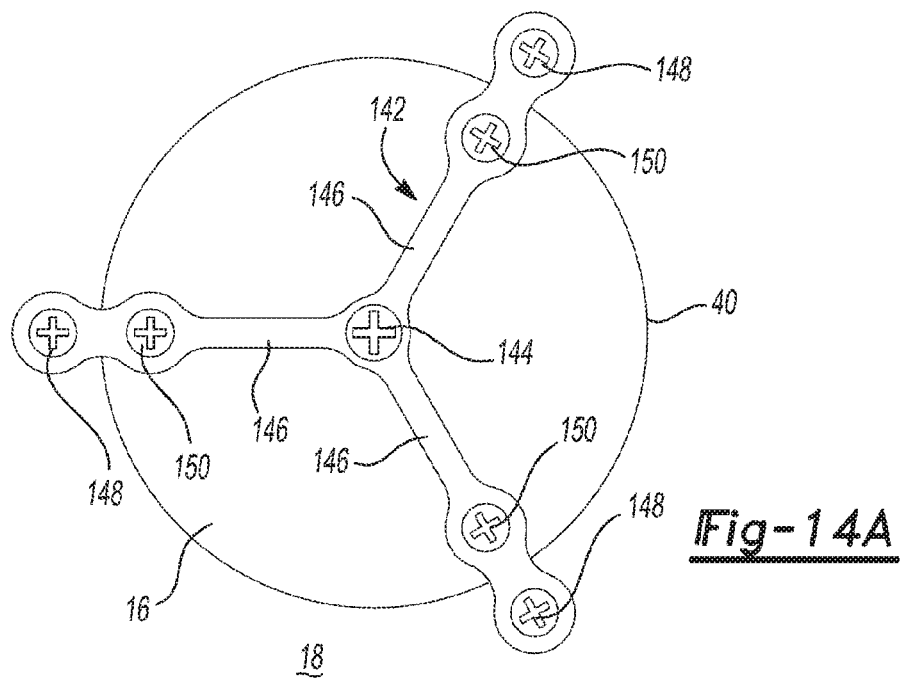
FIG. 14A is a front view of a plate assembly in accordance with the principles of the present disclosure.
Figure 14B:
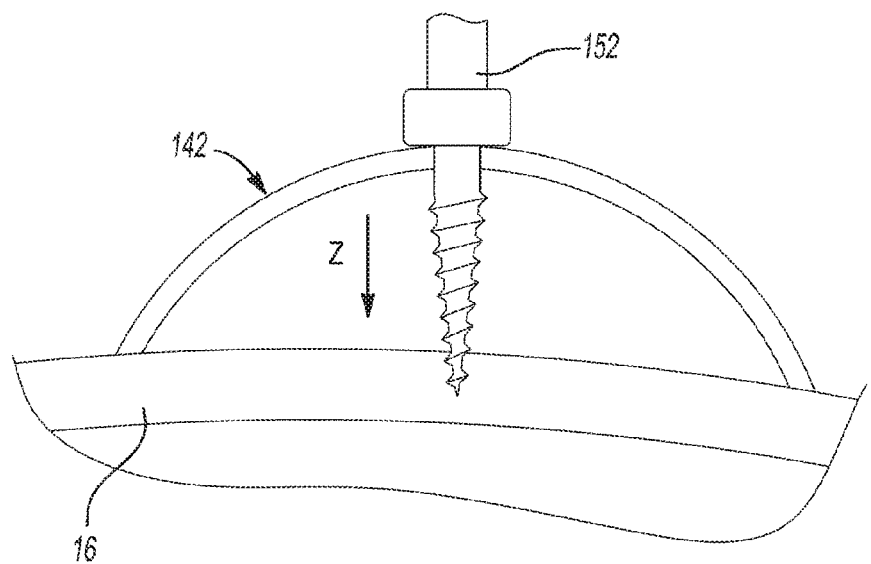
FIG. 14B is a cross-sectional view of the plate assembly of FIG. 14A.

With particular reference to FIGS. 14A and 14B, a plate 142 is shown for use in securing the bone flap 16 relative to the skull 18 following a surgical procedure. The plate 142 may be formed from a flexible material and may include a central aperture 144 and a series of arms 146 radiating from the central aperture 144. The arms 146 may include an aperture located proximate to a distal end of each arm 146 and an aperture 150 located between the aperture 150 and the central aperture 144.

In operation, a fastener 152 may be received by the central aperture 144 and may be inserted into the bone flap 16 to attach the plate 142 to the bone flap 16. As shown in FIG. 14B, the plate 142 may include a substantially arcuate shape in cross-section and may flex in the direction (Z) as the fastener 152 is inserted into the bone flap 16. Allowing the plate 142 to flex in the direction (Z) when the fastener 152 is inserted into the bone flap 16 allows a positive engagement of the arms 146 with the bone flap 16 and the skull 18 when the plate 142 is attached to the bone flap 16 via the fastener 152.

When the plate 142 is attached to the bone flap 16, the apertures 148 may be positioned relative to the skull 18 such that each aperture 148 opposes the skull 18. In this position, the apertures 150 may be positioned over the bone flap 116 such that the apertures 150 oppose the bone flap 16. When the plate 142 is in the position shown in FIG. 14A, the apertures 148 oppose the skull 18 while the apertures 150 oppose the bone flap 16. Accordingly, a portion of each arm 146 that extends between the apertures 148, 150 extends over the cut line 140 and, as a result, joins the bone flap 16 to the skull 18 when fasteners (not shown) are inserted into each of the apertures 148, 150. The position of the apertures 148, 150 relative to the skull 18 and the bone plate 16 may be controlled based on the depth of insertion of the fastener 152 into the bone flap 16. For example, the apertures 148 may extend farther onto the skull 18 and the apertures 150 may extend closer to the cut line 40 when the fastener 152 is driven farther in the direction (Z). Conversely, the apertures 148 may extend closer to the cut line 140 and the apertures 150 may extend in a direction closer to the central aperture 144 when the fastener 152 is driven into the bone flap 16 to a lesser extent in the direction (Z).

Regardless of how far the fastener 152 is driven in the direction (Z), provided the apertures 148 oppose the skull 18 and the apertures 150 oppose the bone flap 16 such that a portion of the arms 146 crosses the cut line 40, when fasteners are respectively inserted into the apertures 148, 150, a position of the plate 142 relative to the skull 18 and relative to the bone flap 16 is achieved. Accordingly, a position of the bone flap 16 relative to the skull 18 is maintained, thereby allowing the bone flap 16 to heal following the surgical procedure.

With particular reference to FIGS. 15A and 15B, a plate 154 is shown for attaching the bone flap 16 to the skull 18. The plate 154 may include a series of retention features 156 for attachment to a series of arms 158 (FIG. 15B). As illustrated, the retention features 156 may open into a peripheral edge of the plate 154.

In operation, the plate 154 may be placed on the skull 18 and the cut line 140 may be determined based on the outer diameter of the plate 154. Namely, the outer diameter of the plate 154 may be used to mark or otherwise score the skull 18 to define the cut line 40. The cut line 40 may be used by the surgeon to cut the portion of the skull 18 that defines the bone flap 16 to allow the surgeon access to the patient's brain. The plate 154 may be attached to the bone flap via a fastener 160 and may be attached prior to or following removal of the bone flap 16 from the skull 18.

The arms 158 may be snapped into the retention features 156 when the bone flap 16 is removed from the skull 18. Alternatively, the arms 158 may be inserted into the retention features 156 after the bone flap 16 is returned to the skull 18. Regardless of when the arms 158 are attached to the retention features 156, the arms 158 may be attached to the skull 18 via a series of fasteners (not shown) respectively received within apertures 162 formed approximate to a distal end of each arm 158. Once the fasteners are inserted into the skull 18, the arms 158 span the cut line 40 and, as a result, fix a position of the plate 154 relative to the skull 18, as the position of the arms 158 is fixed relative to the plate 154 via the retention features 156. Accordingly, a position of the bone flap 16 relative to the skull 18 is fixed and permits the bone flap 16 to heal following the surgical procedure.

With particular reference to FIG. 16, a plate 164 is shown and may include a series of teeth 166. The teeth 166 may interact with a series of teeth 168 respectively associated with a series of arms 170. The arms 170 may each include an attachment aperture 174 located at a distal end of each arm 170. The arms 170 may be moved between a retracted position (FIG. 16) and an extended position when the plate 164 is rotated about a fastener/rivet that rotatably attaches the plate 164 to the bone flap 16.

In operation, the arms 170 may be moved from the retracted position (FIG. 16) to the extended position when the plate 164 is rotated relative to the bone flap 16. Specifically, when the plate 164 is rotated about the rivet 172 relative to the bone flap 16, the teeth 166 of the plate 164 engage the teeth 168 of the arms 170 to cause rotation of each arm 170 into the extended state.

When the arms 170 are in the extended state, a portion of each arm 170 crosses the cut line 40 and positions the attachment apertures 174 over the skull 18. In this position, a fastener (not shown) may be inserted into each aperture 174 to fix a position of each arm 170 relative to the skull 18.

Because each arm 170 is rotatably attached to the plate 164 via a fastener/rivet 176, fixing the arms 170 to the skull 18 via the apertures 174 likewise fixes a position of the bone flap 16 relative to the skull 18. Fixing a position of the bone flap 16 relative to the skull 18 allows the bone flap 16 to heal following a surgical procedure.

Figure 17A:
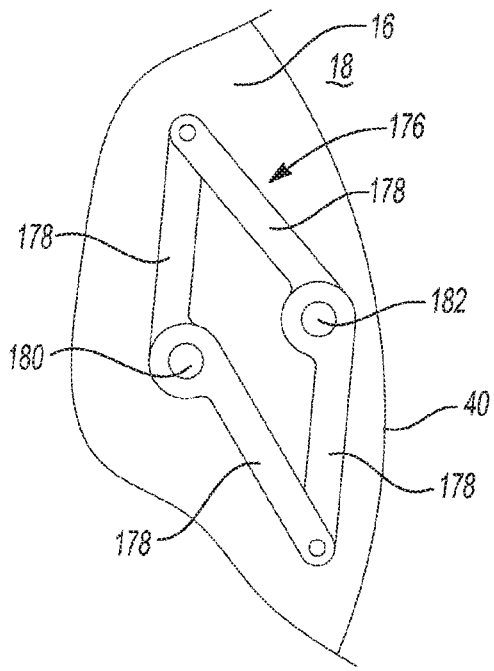
FIG. 17A is a front view of a plate assembly in accordance with the principles of the present disclosure shown in a retracted position.
Figure 17B:
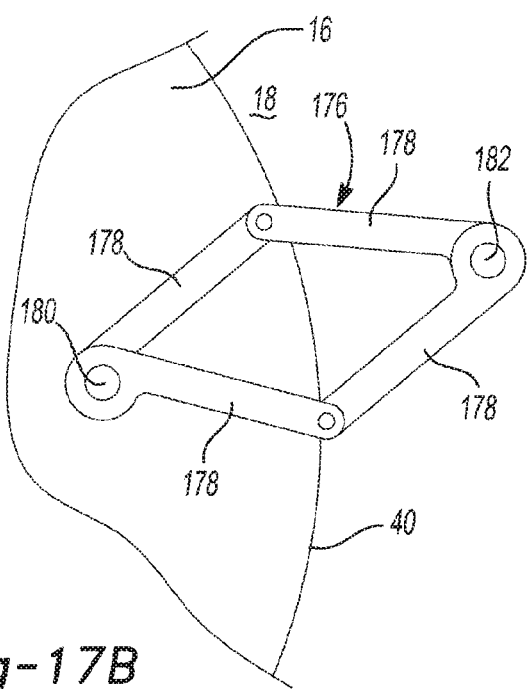
FIG. 17B is a perspective view of the plate assembly of FIG. 17A in an extended position.

With particular reference to FIGS. 17A-17B, a linkage mechanism 176 is provided. The linkage mechanism 176 may include a series of links 178 that are rotatably attached to one another. The linkage mechanism 176 may be attached to the bone flap 16 via a fastener 180 that permits relative rotation of the links 178 relative to the bone flap 16.

In operation, the linkage mechanism 176 may be secured to the bone flap 16 via the fastener 180. A force may then be applied to the linkage mechanism 176 to cause the linkage mechanism 176 to move from the retracted position (FIG. 17A) to the extended position (FIG. 17B). In this position, an attachment aperture 182 associated with two of the links 178 is extended and positioned over the skull 18. A fastener (not shown) may be inserted into the attachment aperture 182 to fix a position of the links 178 relative to the skull 18. Because the linkage mechanism 176 is likewise attached to the bone flap 16 via the fastener 180, fixing the links to the skull 18 via the fastener associated with attachment aperture 182 likewise fixes a position of the bone flap 16 relative to the skull 18. Fixing a position of the bone flap 16 relative to the skull 18 allows the bone flap 16 to heal following a surgical procedure.

Figure 17C:
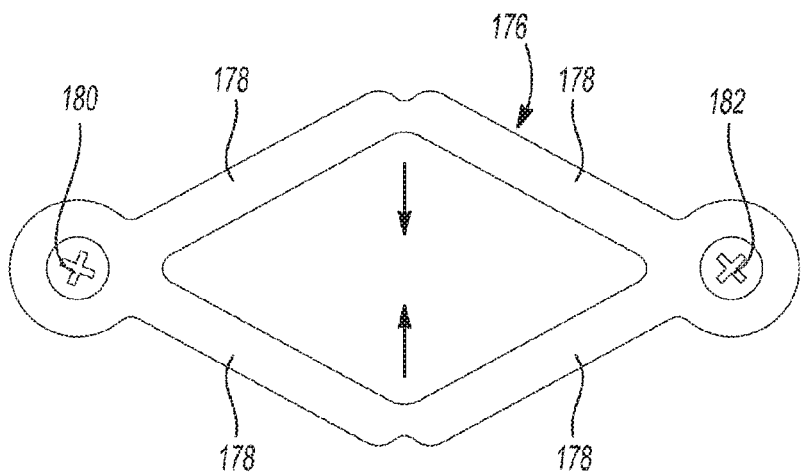
FIG. 17C is a front view of an alternate configuration of the plate assembly of FIG. 17A.

While the linkage mechanism 176 is described as including a series of links 178, the linkage mechanism 178 could alternatively be formed from a flexible material that allows the linkage mechanism 176 to move from the retracted state (FIG. 17A) to the extended state (FIG. 17B) without causing relative, pivotal movement between links. For example, as shown in FIG. 17C, a linkage mechanism 176a may include a substantially unitary construction, whereby links 178a are integrally formed with one another and are movable relative to one another due to the nature of the material used in forming the linkage mechanism 176a. If the linkage mechanism 176a is formed from a unitary construction, the linkage mechanism 176a may be attached at one end to the bone flap 16 via the fastener 180 and may be attached to the skull 18 at a second end via the fastener 182 to secure a position of the bone flap 16 relative to the skull 18.

Figure 18A:
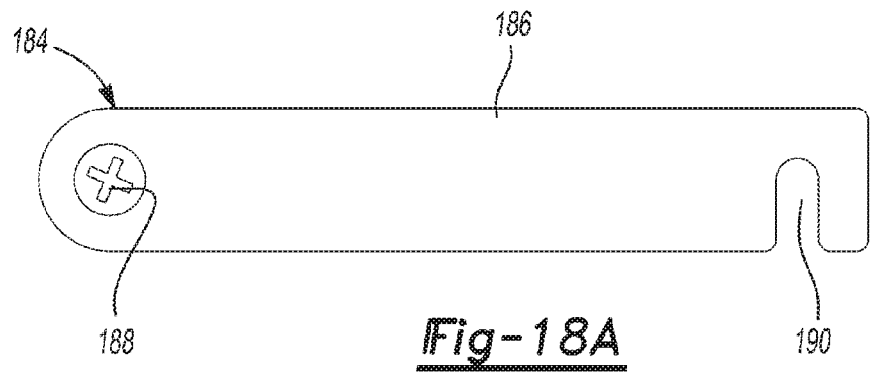
FIG. 18A is a front view of a plate member in accordance with the principles of the present disclosure.
Figure 18B:
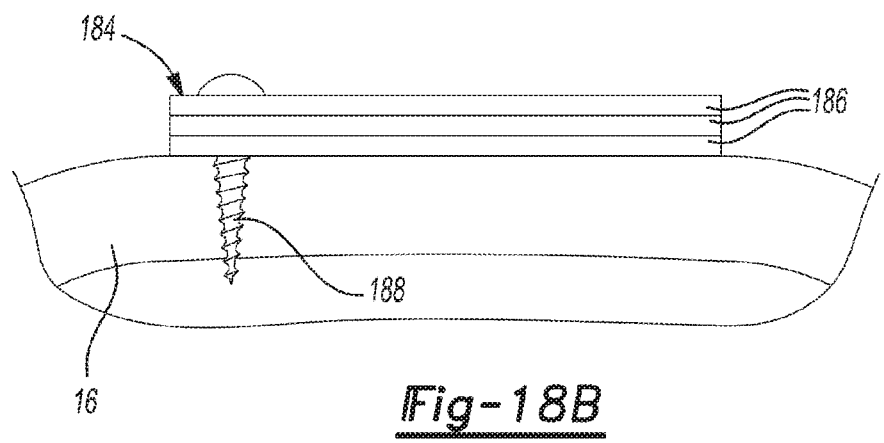
FIG. 18B is a side view of a plate assembly incorporating the plate member of FIG. 18A.
Figure 18C:
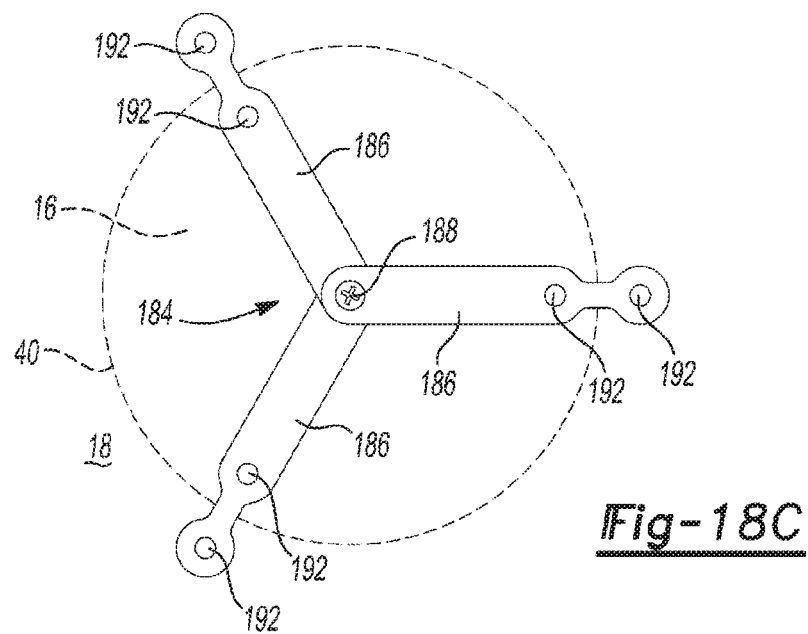
FIG. 18C is a front view of the plate assembly of FIG. 18B shown in an extended position.

With particular reference to FIGS. 18A-18C, a plate assembly 104 is provided for use in securing a bone flap 16 to a skull 18. The plate assembly 184 may include a series of arms 186 that are stacked relative to one another and are rotatably attached to the bone flap 16 via a common fastener 188. Each of the arms 186 may include a cut guide 190 that may be used to define a position of the cut line 40 and, thus, may be used to define a shape of the bone flap 16. Specifically, the plate assembly 184 may be rotatably attached to the bone flap 16 via the fastener 188 and may define a shape of the cut line 40 by inserting a pencil or other marking/scoring device into the cut guide 190. Movement of the pencil or scoring device may be controlled by positioning the pencil/scoring device within the cut guide 190 and applying a force on each arm 186, thereby causing the arms 186 to rotate about and relative to the fastener 188. In so doing, the pencil/scoring device marks a location of the cut line 40 for use by the surgeon in removing the bone flap 16 from the skull 18.

Once the bone flap 16 is severed from the skull 18 at the cut line 40, the bone flap 16 and the plate assembly 184 may be removed from the skull 18 to provide access to the patient's brain. Once a surgical procedure performed on the patient's brain is complete, the plate assembly 184 and bone flap 16 may be returned to the skull 18. At this point, the arms 186 may be rotated relative to one another and relative to the fastener 188 such that the arms 186 are spread apart from one another and are located at different places along the perimeter of the bone flap 16 (FIG. 18C). A series of fasteners (not shown) may be respectively inserted into apertures 192 to fix each arm 186 to the bone flap 16 and to the skull 18 such that a portion of each arm 186 spans the cut line 40. Attaching each arm 186 at one location to the skull 18 and at another location to the bone flap 16 secures a position of each arm 186 and, thus, the plate assembly 184, relative to the bone flap 16 and the skull 18. In so doing, a position of the bone flap 16 relative to the skull 18 is maintained, thereby allowing the bone flap 16 to heal following a surgical procedure.

While the plate assembly 184 is described and shown as including a series of arms 186 that each include a cut guide 190, only one of the arms 186 may be provided with a cut guide 190, as shown in FIG. 19. The arm 186 provided with the cut guide 190 may be used as described above to define the cut line 40 for use by the surgeon in creating the bone flap 16. Regardless of whether the plate assembly 184 includes a series of arms 186 that each include a cut guide 190 (FIGS. 18A-18C) or a series of arms 186, whereby only one of the arms 186 includes a cut guide 190, the arms 186 may be formed from a material that permits each arm 186 to flex when attached to the bone flap 16 and skull 18. Namely, because the arms 186 are stacked on top of one another, as shown in FIG. 18B, when the arms 186 are spread apart from one another, as shown in FIG. 18C, some of the arms 186 are positioned farther from the bone flap 16 and skull 18 than the other arms 186. Accordingly, when the fasteners are inserted into the arms 186, the arms 186 are required to bend to prevent breakage of any of the arms 186 when the arms 186 are attached to the bone flap 16 and skull 18.

If the plate assembly 184 does not include a cut guide 190 associated with any of the arms 186, a separate stencil for such template 194 (FIGS. 20A and 20B) may be used by the surgeon to generate the cut line 40. The template 194 may be attached to the skull 18 via a fastener 196 (FIG. 20C) having a gripping feature 198 that allows a surgeon to manipulate the fastener 196 and, thus, position the template 194 relative to the skull 18. The fastener 196 may be used to maintain a position of the template 194 relative to the skull 18 to allow the surgeon to generate the cut line 40 on the skull 18. Once the cut line 40 is generated, the fastener 196 and template 194 may be removed and the bone flap 16 may be separated from the skull 18.

Figure 21:
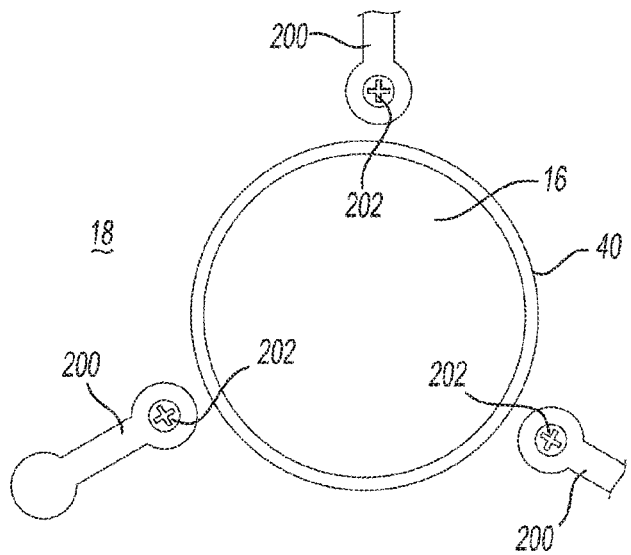
FIG. 21 is a front view of a plate assembly in accordance with the principles of the present disclosure shown in a retracted state.

With particular reference to FIG. 21, a series of separate plates 200 are shown for use in attaching a bone flap 16 to a skull 18. The plates 200 may be first attached to the skull 18 via a series of fasteners 202. The plates 200 may be installed on the skull 18 prior to or following a surgical procedure and may be used to secure the bone flap 16 to the skull 18 once the bone flap 16 is returned to the skull 18 following the surgical procedure.

The plates 200 may be rotated about and relative to the fasteners 202 from the position shown in FIG. 21 to a position where each plate 200 extends over the bone flap 16. Specifically, the plates 200 may be rotated about the fasteners 202 such that a portion of each plate 200 spans the cut line 40 and extends over the bone flap 16. At this point, a fastener may be inserted into each plate 200 at an opposite end than the fastener 202 to secure the plates 200 to the bone flap 16. Securing the plates 200 to the bone flap 16 and to the skull 18 likewise fixes a position of the bone flap 16 relative to the skull 18, thereby allowing the bone flap 16 to heal following a surgical procedure.

Figure 22:
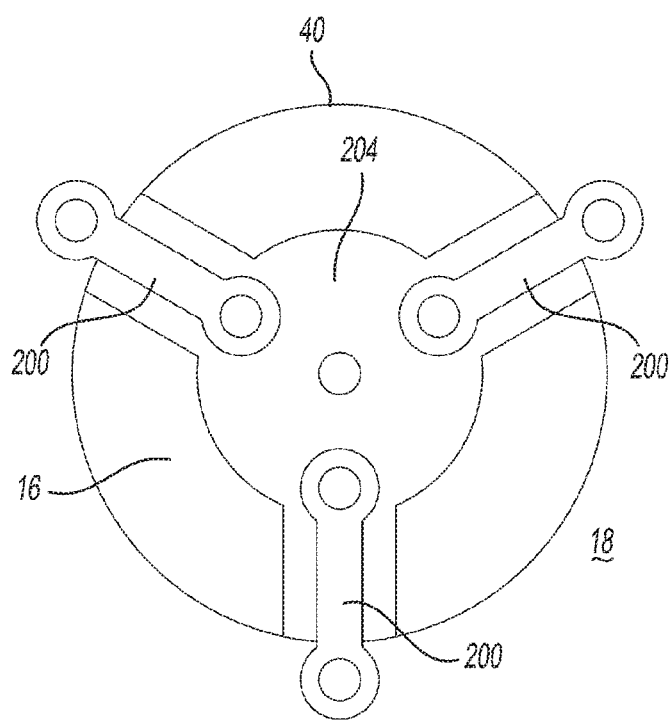
FIG. 22 is a front view of a plate assembly in accordance with the principles of the present disclosure shown in an extended state.

The plates 200 may be used as separate components or, alternatively, may be used in conjunction with a main plate 204, as shown in FIG. 22. Specifically, the plates 200 may be carried by the main plate 204 such that each plate 200 is slidably attached to and carried by the main plate 204. If the plates 200 are carried by the main plate 204, the plates 200 may be moved between an extended position (FIG. 22) and a retracted position (not shown). When the plates 200 are in the retracted position, the plates 200 are separated from the cut line 40 and do not extend over the skull 18. Conversely, when the plates 200 are in the extended position (FIG. 22), a portion of each plate 200 extends over the cut line 40 such that each plate 200 is secured at one end to the skull 18 and is secured at another end to the bone flap 16. Securing the plates 200 to the bone flap 16 and to the skull 18 likewise secures a position of the bone flap 16 relative to the skull 18, thereby allowing the bone flap 16 to heal following a surgical procedure.

With particular reference to FIGS. 23-31, a plate assembly 206 for use in securing a bone flap 16 to a skull 18 is provided. The plate assembly 206 may include a main plate 208 and a series of attachment plates 210 rotatably attached to and supported by the main plate 208. The main plate 208 may include a central aperture 212 as well as a series of arms 214 radiating from the central aperture 212. Each arm 214 may include a collar 216 rotatably supported relative to each arm 214 proximate to a distal end of each arm 214.

Figure 26:
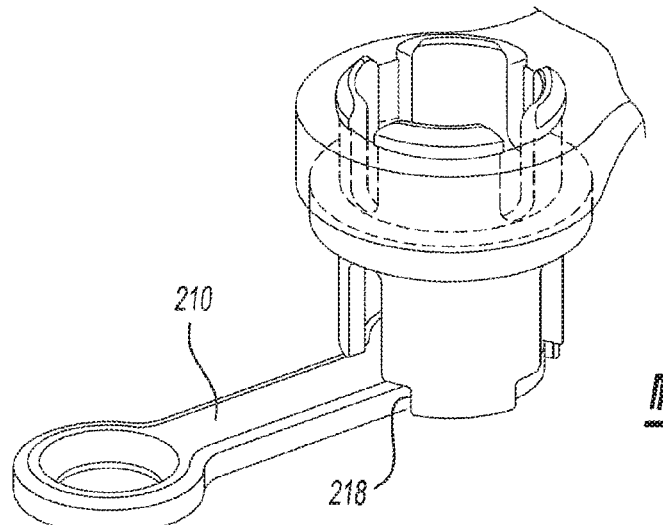
FIG. 26 is a partial perspective view of the plate assembly of FIG. 24.
Figure 27:
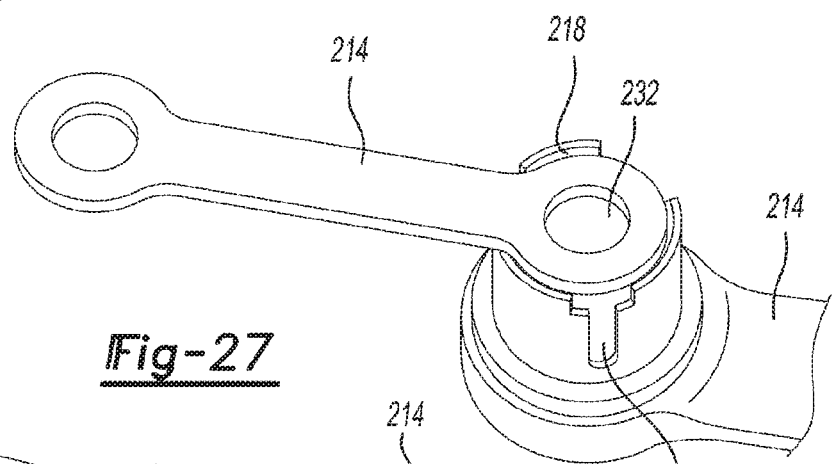
FIG. 27 is a partial perspective view of the plate assembly of FIG. 24.
Figure 28:
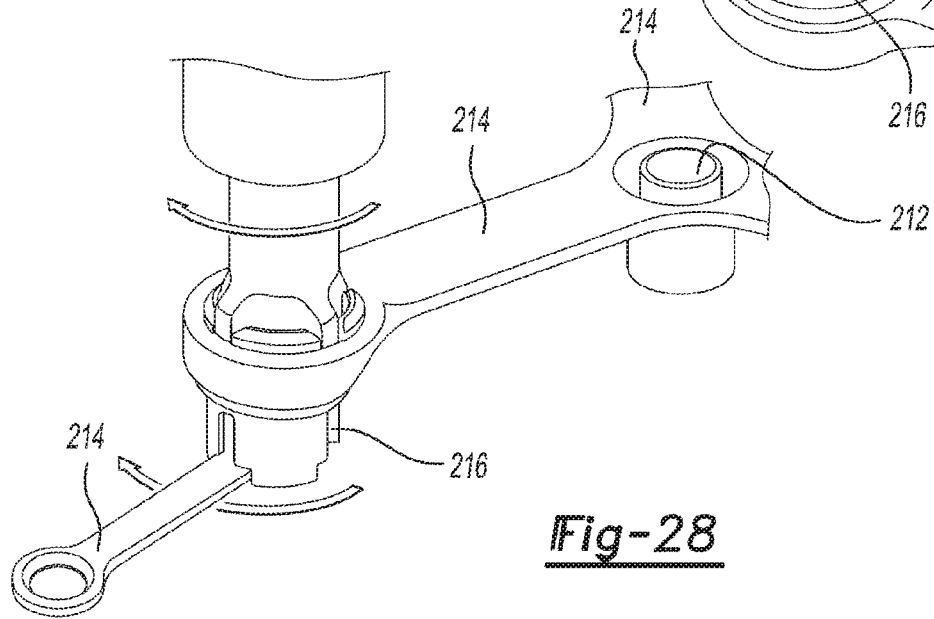
FIG. 28 is a partial perspective view of the plate assembly of FIG. 24 showing the tool of FIG. 25 rotating a portion of the plate assembly of FIG. 24.
Figure 29:
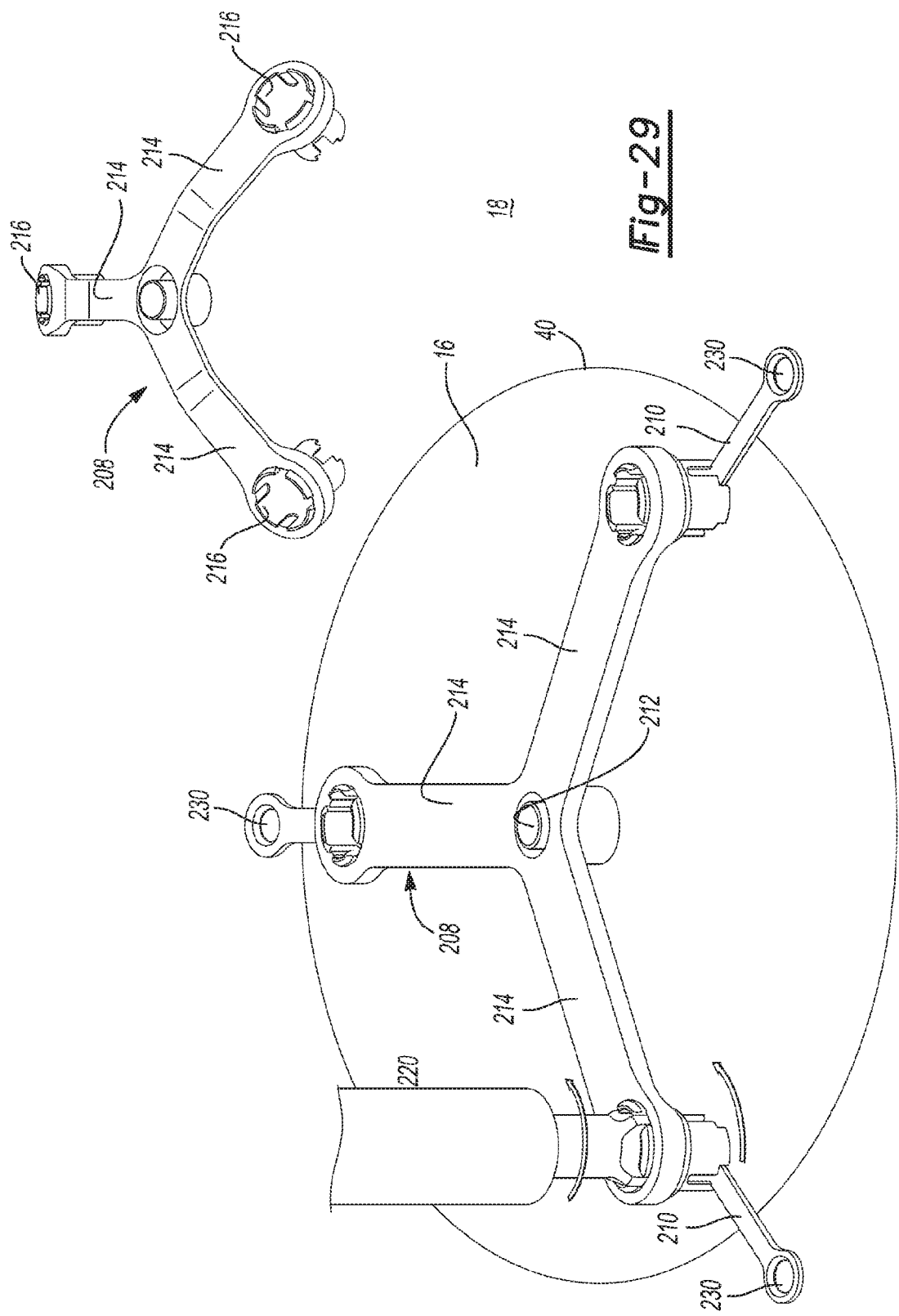
FIG. 29 is a perspective view of the plate assembly of FIG. 24 showing the tool of FIG. 25 during installation of the plate assembly of FIG. 24.

As shown in FIGS. 26 and 27, the collars 216 may include a key feature 218 that matingly receives one end of a respective attachment plate 210 to fix the attachment plate 210 for movement with the collar 216.

In operation, the main plate 208 may receive a series of attachment plates 210 at the collars 216. Specifically, the attachment plates 210 may be inserted into the key feature 218 to fix the attachment plates 210 for rotation with the respective collars 216 via the key features 218 of each collar 216.

The main plate 208 may first be positioned relative to the bone flap 16 by inserting an installation tool 220 into the central aperture 212. Specifically, a threaded end 222 of the installation tool 220 may threadably engage the central aperture 212 of the main plate 208. Threadably engaging the end 222 of the installation tool 220 with the central aperture 212 of the main plate 208 fixes the main plate 208 for movement with the installation tool 220. The installation tool 220 may include a gripping feature 224 that aides a surgeon in grabbing and manipulating the installation tool 220 during use. Because the main plate 208 is fixed for movement with the installation tool 220 via the threaded end 222 of the installation tool 220 and the central aperture 212 of the main plate 208, movement of the installation tool 220 likewise causes movement of the main plate 208 relative to the bone flap 16.

The installation tool 220 may be used to position the main plate 208 relative to the bone flap 16 until a desired position of the main plate 208 is achieved. At this point, the installation tool 220 may be removed and a fastener (not shown) may be inserted into the central aperture 212 to fix a position of the main plate 208 relative to the bone flap 16.

Once the main plate 208 is fixed to the bone flap 16, a second end 226 may be respectively and individually inserted into the collars 216. Specifically, the second end 226 of the installation tool 224 may include an engagement feature 228 that is matingly received by the collars 216. Accordingly, when the engagement feature 228 is inserted into the respective collars 216, rotation of the installation tool 224 likewise causes rotation of the collars 216 relative to the arms 214 of the main plate 208.

Rotation of the collars 216 relative to the main plate 208 likewise causes rotation of the attachment plates 210 relative to the main plate 208 and relative to the bone flap 16, as the attachment plates 210 are fixed for movement with the collars 216 via the key feature 218 of the collars 216. The rotational force supplied to each collar 216 via the installation tool 224 may cause each attachment plate 210 to be rotated into the extended position (FIG. 24) such that the attachment plates 210 extend over the cut line 40 and an attachment aperture 230 of each attachment plate 210 extends over the skull 18. A fastener (not shown) may be inserted into the attachment aperture 230 of each attachment plate 210 to fix each attachment plate 210 to the skull 18. A similar fastener may be inserted into the collar 216 and, subsequently, through an attachment aperture 232 (FIG. 27) of the attachment plates 210 to fix the attachment plates 210 to the bone flap 16.

As described, the attachment plates 210 may be rotated by the installation tool 220 via interaction between the installation tool 220 and the collars 216. Once the collars 216 are sufficiently rotated relative to each arm 214 such that the attachment plates 210 extend over the cut line 40, fasteners may be inserted into the attachment apertures 230, 232, of the attachment plates 210 to fix the attachment plates 210 at one end to the skull 18 and at another end to the bone flap 16. Fixing the attachment plates 210 to the bone flap 16 and to the skull 18 likewise fixes a position of the bone flap 16 to the skull 18 and, as a result, allows the bone flap 16 to heal following a surgical procedure.

While the fasteners are described as being inserted into the apertures 232 of the attachment plates 210 following insertion of the fasteners into the attachment apertures 230, the fasteners associated with the attachment apertures 232 may first be inserted into the bone flap 16 prior to the fasteners being inserted into the fasteners 232. In fact, the fasteners may be inserted into the attachment apertures 230 of the attachment plate 210 to attach each attachment plate 210 to the bone flap 16 prior to the bone flap 16 being removed from the skull 18. The fasteners may be inserted into the apertures 230 to attach the arms 214 of the main plate 208 as well as the attachment plates 210 to the bone flap 16 prior to removal of the bone flap 16 from the skull 18. While the fasteners are described as attaching the arms 214 of the main plate 208 as well as the attachment plates 210—at the attachment apertures 232—to the bone flap 16, insertion of the fasteners into the attachment apertures 232 permits rotation of the attachment plates 210 relative to the bone flap 16 to permit the installation tool 220 to selectively rotate the attachment plates 210 relative to the bone flap 16 via the collars 216.

Figure 30:
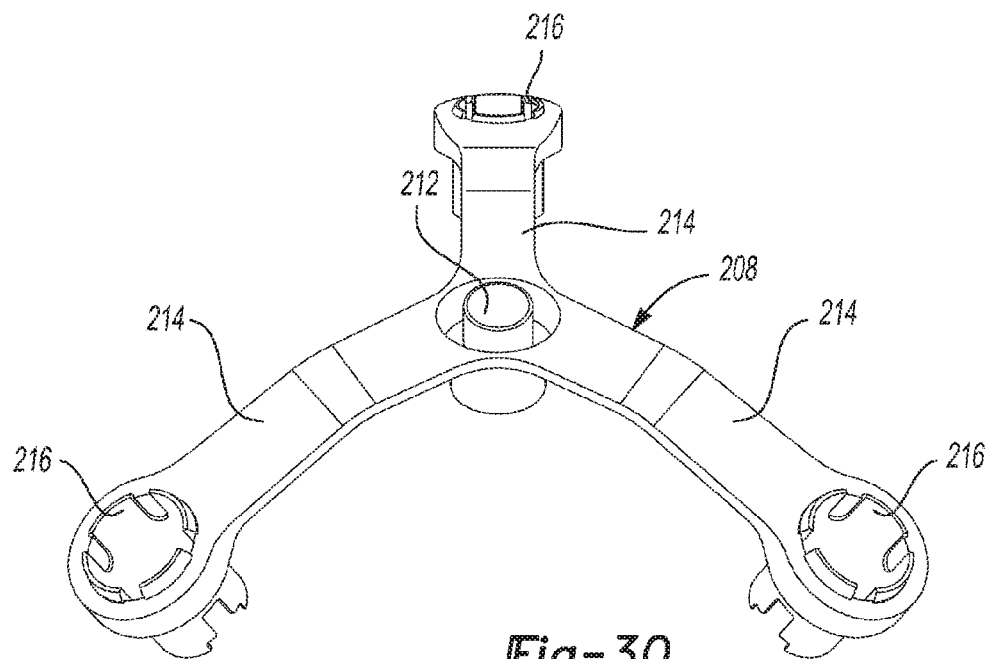
FIG. 30 is a partial perspective view of a plate assembly in accordance with the principles of the present disclosure.
Figure 31:
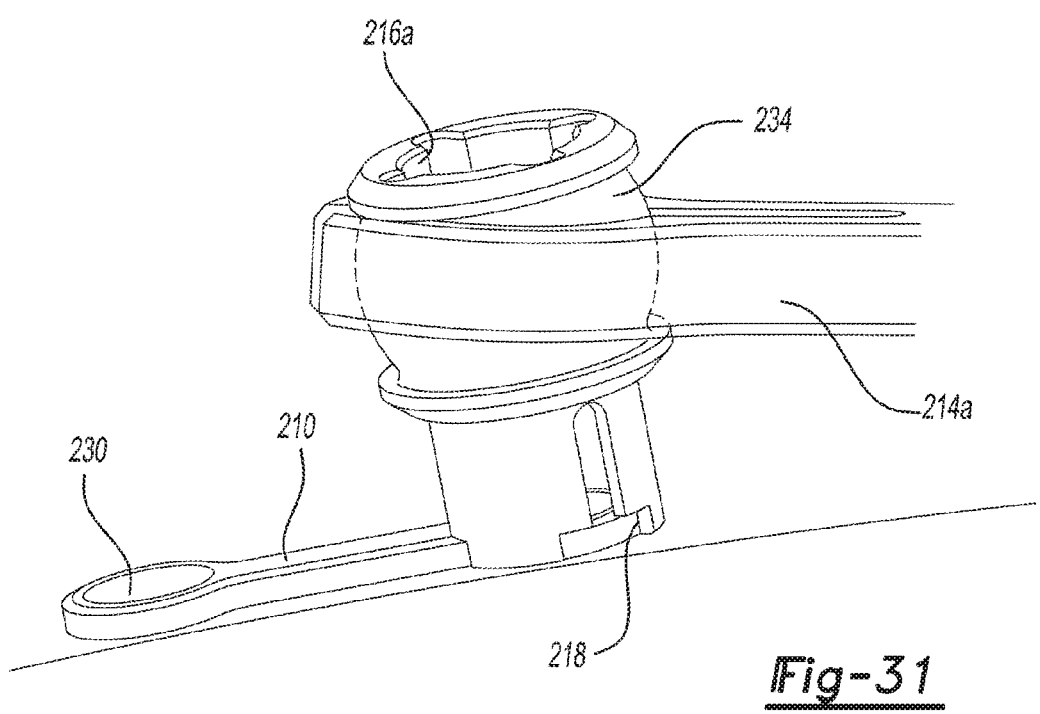
FIG. 31 is a partial perspective view of the plate assembly of FIG. 30 incorporating a movable plate and collar assembly.

With particular reference to FIGS. 30 and 31, the main plate 208 is shown as including a flexible feature to allow normalization of the arms 214 of the main plate 208 against the skull 18 when the fastener (not shown) is inserted into the central aperture 212. Namely, when the fastener draws the main plate 208 toward the bone flap 16, the arms 214 may flex to permit such movement of the main plate 208 toward the bone flap 16 at the central aperture 212. Normalization of the main plate 208 relative to the bone flap 16 may further be enhanced by attaching a collar 216a to the distal end of each arm 214a via a ball-and-socket joint 234 (FIG. 31). The ball-and-socket joint 234 permits rotation of the collar 216a relative to the arm 214a and concurrently allows the collar 216a to pivot about the ball-and-socket joint 234.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A plate assembly for attaching a bone flap to a skull, the plate assembly comprising:
   a first plate member operable to be attached to the bone flap;
   a second plate member supported by said first plate member and movable about a first axis of rotation between a retracted position and an extended position relative to the first plate member, said second plate member configured to be removed from a cut line between the bone flap and the skull in said retracted position and configured to extend over a portion of said bone flap, a portion of said skull, and said cut line in said extended position, the second plate member including:
     a first aperture operable to receive a first fastener to secure said second plate member to the bone flap when said second plate member is in said extended position,
     a second aperture operable to receive a second fastener to secure said second plate member to the skull when said second plate member is in said extended position, and a marking feature operable to mark said cut line, said marking feature disposed between said first aperture and said second aperture; and a third plate member movable about a second axis of rotation between a retracted position and an extended position relative to the first plate member, wherein the second plate and the third plate are independently movable, wherein the first axis of rotation is angled relative to the second axis of rotation;

wherein the plate assembly is configured to maintain an orientation and position of the bone flap relative to the skull when attached to the skull in said extended position.

2. The plate assembly of claim 1, wherein said second plate member is pivotably supported by said first plate member between said retracted position and said extended position.

3. The plate assembly of claim 2, wherein said first plate member includes a surface configured to attach to the bone flap, said second plate member pivoting between said retracted position and said extended position about an axis extending substantially parallel to said surface.

4. The plate assembly of claim 1, wherein said second plate member includes a reduced-width portion between said first aperture and said second aperture.

5. The plate assembly of claim 4, wherein said reduced-width portion is configured to extend over said cut line.

6. The plate assembly of claim 1, wherein said first plate member includes an aperture operable to receive a fastener to secure said first plate member to the bone flap.

7. The plate assembly of claim 1, wherein the third plate member is supported by said first plate member and movable between a retracted position and an extended position relative to the first plate member, the third plate member configured to be removed from the cut line between the bone flap and the skull in the retracted position and configured to extend over said cut line in said extended position.

* * * * *